United States Patent
Sethi et al.

(10) Patent No.: US 7,115,625 B2
(45) Date of Patent: *Oct. 3, 2006

(54) TREATMENT OF CARDIOVASCULAR AND RELATED PATHOLOGIES

(75) Inventors: Rajat Sethi, Winnipeg (CA); Wasimul Haque, Edmonton (CA)

(73) Assignee: Medicure International Inc., (BB)

( * ) Notice: Subject to any disclaimer, the term of this patent is extended or adjusted under 35 U.S.C. 154(b) by 0 days.

This patent is subject to a terminal disclaimer.

(21) Appl. No.: 10/639,950

(22) Filed: Aug. 12, 2003

(65) Prior Publication Data

US 2004/0033992 A1 Feb. 19, 2004

Related U.S. Application Data

(62) Division of application No. 09/645,237, filed on Aug. 24, 2000, now Pat. No. 6,677,356.

(60) Provisional application No. 60/150,415, filed on Aug. 24, 1999.

(51) Int. Cl.
*A61K 31/44* (2006.01)
*A61K 31/535* (2006.01)

(52) U.S. Cl. .............. 514/302; 514/233.8; 514/252.01; 514/252.16; 514/252.17; 514/345; 514/351; 514/620

(58) Field of Classification Search ................ 514/321, 514/320, 317, 327, 233.8, 302, 654, 620, 514/252.01, 252.16, 252.17, 345, 350, 351, 514/355

See application file for complete search history.

(56) References Cited

U.S. PATENT DOCUMENTS

| | | | |
|---|---|---|---|
| 3,206,463 A | 9/1965 | Baetz | |
| 3,282,778 A * | 11/1966 | Lohel | 514/161 |
| 3,910,921 A | 10/1975 | Esanu | |
| 3,987,177 A | 10/1976 | Giudicelli et al. | |
| 4,032,534 A | 6/1977 | Chodkiewicz | |
| 4,036,844 A | 7/1977 | Thorne et al. | |
| 4,053,607 A | 10/1977 | Thorne et al. | |
| 4,137,316 A | 1/1979 | Esanu | |
| 4,167,562 A | 9/1979 | Evers | |
| 4,361,570 A | 11/1982 | Fici | |
| 4,369,172 A | 1/1983 | Schor et al. | |
| 4,374,841 A | 2/1983 | Descamps et al. | |
| 4,515,771 A | 5/1985 | Fine | |
| 4,567,179 A | 1/1986 | Lombardino | |
| 4,569,938 A | 2/1986 | Esanu | |
| 4,569,939 A | 2/1986 | Esanu | |
| 4,581,363 A | 4/1986 | Esanu | |
| 4,605,741 A | 8/1986 | Zagnoli et al. | |
| 4,730,042 A | 3/1988 | Hege et al. | |
| 4,735,950 A | 4/1988 | Esanu | |
| 4,735,956 A | 4/1988 | Baldwin et al. | |
| 4,837,239 A | 6/1989 | Benjamin et al. | |
| 4,843,071 A | 6/1989 | Hohenwarter | |
| 4,962,121 A | 10/1990 | Hamberger et al. | |
| 5,001,115 A | 3/1991 | Sloan | |
| 5,053,396 A | 10/1991 | Blass | |
| 5,118,505 A | 6/1992 | Költringer | |
| 5,130,324 A | 7/1992 | Ulrich et al. | |
| 5,132,115 A | 7/1992 | Wolter et al. | |
| 5,210,083 A | 5/1993 | Pfirrmann | |
| 5,213,813 A | 5/1993 | Kornecki et al. | |
| 5,254,557 A | 10/1993 | Buckle et al. | |
| 5,254,572 A | 10/1993 | Serfontein | |
| 5,272,165 A | 12/1993 | Ulrich et al. | |
| 5,278,154 A | 1/1994 | Lacoste et al. | |
| 5,288,498 A | 2/1994 | Stanley et al. | |
| 5,288,716 A | 2/1994 | Speck | |
| 5,326,757 A | 7/1994 | Demopoulos | |
| 5,328,453 A | 7/1994 | Sibalis | |
| 5,372,999 A | 12/1994 | Schneider et al. | |
| 5,385,937 A | 1/1995 | Stamler et al. | |
| 5,420,112 A | 5/1995 | Lewis et al. | |
| 5,441,972 A | 8/1995 | Ogata et al. | |
| 5,504,090 A | 4/1996 | Neely | |
| 5,563,126 A | 10/1996 | Allen et al. | |
| 5,569,459 A | 10/1996 | Shlyankevich | |
| 5,569,648 A | 10/1996 | Lewis et al. | |
| 5,631,271 A | 5/1997 | Serfontein | |
| 5,633,228 A | 5/1997 | Lewis et al. | |
| 5,648,335 A | 7/1997 | Lewis et al. | |
| 5,728,684 A | 3/1998 | Cheng et al. | |
| 5,733,884 A | 3/1998 | Barbul et al. | |
| 5,733,916 A | 3/1998 | Neely | |
| 5,770,215 A | 6/1998 | Moshyedi | |
| 5,795,873 A | 8/1998 | Allen | |
| 5,804,163 A | 9/1998 | Gibby et al. | |
| 5,804,594 A | 9/1998 | Murad | |
| 5,833,998 A | 11/1998 | Biedermann et al. | |
| 5,834,446 A | 11/1998 | Dow et al. | |

(Continued)

FOREIGN PATENT DOCUMENTS

BE 831350 1/1976

(Continued)

OTHER PUBLICATIONS

DiPiro, Editor-in-Chief, PHARMACOTHERAPY, A Pathophysiologic Approach, 1989, pp. 115-118.*

(Continued)

*Primary Examiner*—Dwayne Jones
(74) *Attorney, Agent, or Firm*—Merchant & Gould P.C.

(57) ABSTRACT

Methods for treating cardiovascular and related diseases such congestive heart failure are described. The methods are directed to concurrently administering a compound such as pyridoxal-5'-phosphate, pyridoxamine, pyridoxal, or a 3-acylated pyridoxal analogue with a therapeutic cardiovascular compound.

12 Claims, 34 Drawing Sheets

U.S. PATENT DOCUMENTS

| | | | |
|---|---|---|---|
| 5,840,685 | A | 11/1998 | Fujii et al. |
| 5,847,008 | A | 12/1998 | Doebber et al. |
| 5,858,017 | A | 1/1999 | Demopulos et al. |
| 5,859,051 | A | 1/1999 | Adams et al. |
| 5,874,420 | A | 2/1999 | Pelleg |
| 5,874,443 | A | 2/1999 | Kiely et al. |
| 5,888,514 | A | 3/1999 | Weisman |
| 6,043,259 | A * | 3/2000 | Dhalla et al. ............... 514/345 |
| 6,066,659 | A | 5/2000 | Speck |
| 6,339,085 | B1 * | 1/2002 | Haque ..................... 514/233.8 |
| 6,780,997 | B1 | 8/2004 | Haque |
| 6,890,943 | B1 * | 5/2005 | Haque ........................ 514/350 |

FOREIGN PATENT DOCUMENTS

| | | |
|---|---|---|
| CA | 2 123 935 A | 12/1994 |
| CH | 561183 | 4/1975 |
| DE | 1 958 226 | 5/1970 |
| DE | 24 61 742 A | 7/1976 |
| DE | 863754 | 5/1978 |
| DE | 28 45 484 A | 11/1978 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 11/1987 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1 323 941 | 12/1963 |
| FR | 5552 M | 12/1967 |
| FR | 5801 M | 3/1968 |
| FR | 6453 M | 12/1968 |
| FR | 1 579 544 | 8/1969 |
| FR | 2034539 | 12/1970 |
| FR | 2 101 010 | 3/1972 |
| FR | 2255883 | 7/1975 |
| FR | 2428640 | 1/1980 |
| FR | 2 641 189 A | 7/1990 |
| GB | 1 013 939 | 12/1965 |
| GB | 1 201 014 | 8/1970 |
| GB | 1 297 080 | 11/1972 |
| GB | 1 360 536 | 7/1974 |
| GB | 1 493 993 | 12/1977 |
| GB | 2 254 556 A | 10/1992 |
| JP | 48-21959 | 7/1973 |
| JP | 54-17130 | 2/1979 |
| WO | WO 83/00085 | 1/1983 |
| WO | WO 91/19500 | 12/1991 |
| WO | WO 94/18965 | 9/1994 |
| WO | WO 98/19690 | 5/1998 |
| WO | WO 9819690 A1 * | 5/1998 |
| WO | WO 99/03365 | 1/1999 |
| WO | WO 99/53928 | 10/1999 |
| WO | WO 00/53606 | 9/2000 |
| WO | WO 02/36109 A2 | 5/2002 |

OTHER PUBLICATIONS

Hardman, J. G., Editor-in-Chief, Goodman & Gilman's The Pharmacological Basis of Therapeutics, 9$^{TH}$ Edition, pp. 809, 820-836, 1561-1563, 1568-1571, 1573, and 1585-1588, 1996.*

Aybak, M. et al., "Effect of Oral Pyridoxine Hydrochloride Supplementation on Arterial Blood Pressure in Patients with Essential Hypertension", Arzneim.-Forsch./Drug Res. 45 (II), pp. 1271-1273, Nr. 12 (1995).

"B Vitamins May Cut Heart Diseas Risk", Harvard Health Letter, 1 page (1998).

Baliga, B. et al., "Hyperhomocysteinemia in Type 2 Diabetes Mellitus: Cardiovascular Risk Factors and Effect of Treatment with Folic Acid and Pyridoxine", Endocrine Practice, vol. 6, No. 6, pp. 435-441 (Nov./Dec. 2000).

Barrett, S., "Homocysteine: A Cardiovascular Risk Factor Worth Considering", http://www.quackwatch.com/03HealthPromotion/homocysteine.html, 2 pages ( © 1997).

Berger, A.R. et al., "Dose response, coasting, and differential fiber vulnerability in human toxic neuropathy: A prospective study of pyridoxine neurotoxicity", Neurology, vol. 42, No.7, pp. 1367-1370 (Jul. 1992).

Bernstein, A., "Vitamin $B_6$ in Clinical Neurology", Annals of New York Academy of Sciences, vol. 585, pp. 250-260 (1990).

Bhagavan, H. et al., "Effect of Postweanling Pyridoxine Deficiency on Growth and Concentration of the Coenzyme Pyridoxal-5'-phosphate in Heart, Kidneys, Lungs, and Adrenals in Rats", Pediat. Res., vol. 10, pp. 730-732 (1976).

Bode, W. et al., "Pyridoxal-5'-Phosphate and Pyridoxal Biokinetics in Male Wistar Rats Fed Graded Levels of Vitamin B-6", J. Nutr., vol. 121, No. 11, pp. 1738-1745 (Nov. 1991).

Chasan-Taber, L. et al., "A Prospective Study of Folate and Vitamin $B_6$ and Risk of Myocardial Infarction in US Physicians", Journal of the American College of Nutrition, vol. 15, No. 2, pp. 136-143 (Apr. 1996).

Cho, Y. et al., "In Vivo Evidence for a Vitamin B-6 Requirement in Carnitine Synthesis", J. Nutr., vol. 120, pp. 258-265 (1990).

"Computer Generated Search Reports", 70 pages (May 1999).

Dakshinamurti, K. et al., Hypertension, calcium channel and pyridoxine (vitamin B6), Abstract to Molecular and Cellular Biochemistry, vol. 188, No. 1-2, pp. 137-148 (Nov. 1998).

Ellis, J. et al., "Prevention of Myocardial Infarction by Vitamin $B_6$", Res. Commun. Molec. Pathol. Pharmacol., vol. 89, No. 2, pp. 208-220 (Aug. 1995).

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", Circulation, vol. 98, pp. 204-210 (Jul. 21, 1998).

Folsom, Aaron R. et al., "Prospective Study of Coronary Heart Disease Incidence in Relation to Fasting Total Homocysteine, Related Genetic Polymorphisms, and B Vitamins", The Atherosclerosis Risk in Communities (ARIC) Study, pp. 204-210, Dec. 15, 1997.

Fragley, M. et al., "Effect of Pyridoxine and Tryptophan, Alone and Combined, on the Development of Deoxycorticosterone Acetate-Induced Hypertension in Rats," Pharmacology, vol. 50, pp. 298-306 (1995).

Harada, K. et al., "Studies on Vitamin $B_6$. (IV) Behavior of Pyridoxal Acylates in the Body After Parenteral Administration", Vitamins Journal of the Vitamin Society of Japan, vol. 45, No. 2, pp. 69-75 (Feb. 1972).

Hoover, D.M. et al., "Ultrastructural Lesions of Pyridoxine Toxicity in Beagle Dogs", Vet. Pathol., vol. 18, pp. 769-777 (1981).

Kok, F. et al., "Low Vitamin $B_6$ Status in Patients with Acute Myocardial Infarction", Am. J. Cardiol., vol. 63, pp. 513-516 (Mar. 1, 1989).

Korytnyk et al. Schiff Based of Pyridoxal: Their Structure and the Stabilization of their Ring-Chain Tautomeric Forms by Acylation, Tetrahedron, 26 (23), 5415-25.

Krinke, G. et al., "Pyridoxine Megavitaminosis: An Analysis of the Early Changes Induced with Massive Doses of Vitamin $B_6$ in Rat Primary Sensory Neurons", J. Neuropathol. Exp. Neurol., vol. 44, No. 7, pp. 117-129 (Mar. 1985).

Kubyshkin, V. et al., "Comparative characteristics of the arrhythmic syndrome and the possibility for its coenzyme correction in dilated and hypertrophic cardiomyopathy", Abstract, 1 pg. (1989).

Lal, K. et al., "Calcium channels in vitamin $B_6$ deficiency-induced hypertension", Journal of Hypertension, vol. 11, No. 12, pp. 1357-1362 (Dec. 1993).

Lal, K. et al., "Hypotensive action of 5-HT receptor agonists in the vitamin $B_6$-deficient hypertensive rat", Eur. J. Pharmacol., vol. 234, Nos. 2/3, pp. 183-189 (Apr. 1993).

Lal, K. et al., "The effect of vitamin B$_6$ on the systolic blood pressure of rats in various animal models of hypertension", *Journal of Hypertension*, vol. 14, No. 3, pp. 355-363 (Mar. 1996).

Levy, Howard A. et al., "Pyridoxine Deficiency in Congestive Heart Failure", *Proceedings of the Society for Experimental Biology and Medicine* vol. 101, pp. 617-621 (Aug. 1959).

Manore, M. et al., "Changes In Plasma Pyridoxal Phosphate (PLP) In Diabetic (D), Hypertensive (HTN) and Hypertensive-diabetic (HTN-D) Men Fed A Constant Vitamin B-6 (B6) Diet", *Source Unknown*, pp. 1254, date unknown.

Mendelsohn, A. et al., "Hemodynamic and Clinical Effects of Oral Levodopa in Children With Congestive Heart Failure", *JACC*, vol. 30, No. 1, pp. 237-242 (Jul. 1997).

Merrill, Jr. et al. A. et al., "Diseases associated with defects in vitamin B$_6$ metabolism or utilization", *Ann. Rev. Nutr.*, vol. 7, pp. 137-156 (1987).

Mulvaney, D. et al., "Electrocardiographic changes in vitamin B$_6$ deficient rats", *Cardiovascular Research*, vol. 13, pp. 506-513 (1979).

Omenn, G. et al., "Preventing Coronary Heart Disease", *Circulation*, vol. 97, pp. 421-424 (1998).

Paulose, C. et al., "Sympathetic Stimulation and Hypertension in the Pyridoxine-Deficient Adult Rat", *Hypertension*, vol. 11, No. 4, pp. 387-391 (Apr. 1988).

Rao, R. et al., "Failure of Pyridoxine to Improve Glucose Tolerance in Diabetics", *Journal of Clinical Endocrinology & Metabolism*, vol. 50, No. 1, pp. 198-200 (Jan. 1980).

Rimm, Eric B. et al., "Folate and Vitamin B$_6$ From Diet and Supplements in Relation to Risk of Coronary Heart Disease Among Women", *Journal of American Medical Association*, vol. 279, No. 5, pp. 359-364, Feb. 4, 1998.

Sakuragi, T. et al., "The Synthesis of Long Chain Fatty Acid Derivatives of the Vitamin B$_6$ Group", *J. Am. Chem. Soc.*, vol. 78, pp. 839-842 (Feb. 20, 1956).

Takuma, Y. et al., "Combination Therapy of Infantile Spasms With High-Dose Pyridoxal Phosphate and Low-Dose Corticotropin", *Journal of Child Neurology*, vol. 11, No. 1, pp. 35-40 (Jan. 1996).

Tanaka, T. et al., "Pyridoxine Derivatives", *Chemical Abstracts*, vol. 62, No. 12, 1 page (Jun. 7, 1965).

Trezise, D. et al., "P$_2$ purinoceptor antagonist properties of pyridoxal-5-phosphate", *Eur. J. Pharmacol.*, vol. 259-300 (Jul. 11, 1994).

Vasudev, Sindhu C. et al., "Glutaraldehyde-treated Bovine Peridcardium: Changes in Calcification due to Vitamins and Platelet Inhibitors", *Artif. Organs*, 21(9), 1007-1013, (1997).

Verhoef, P. et al., "Homocysteine Metabolism and Risk of Myocardial Infarction: Relation with Vitamins B$_6$, B$_{12}$, and Folate", *Am. J. Epidemiol.*, vol. 143, No. 9, pp. 845-859 (May 1, 1996).

Vermaak, W.J.H. et al., "Vitamin B$_6$ and coronary artery disease. Epidemiological observations and case studies", *Atherosclerosis*, vol. 63, pp. 235-238 (Feb. 1987).

Vidrio, H., "Interaction with Pyridoxal as a Possible Mechanism of Hydralazine Hypotension", *Journal of Cardiovascular Pharmacology*, vol. 15, pp. 150-156 (1990).

Viscontini, V. et al., "Über einige Derivate des pyridoxals", *Helvetica Chimica Acta*, vol. 34, No. 296, pp. 2438-2439 (1951).

Windebank, A., "Neurotoxicity of Pyridoxine Analogs Is Related to Coenzyme Structure", *Neurochemical Pathology*, vol. 3, pp. 159-167 (1985).

Yarat, A. et al., "Effect of vitamin B6 on lenses of diabetic rats", *Indian Journal of Experimental Biology*, vol. 36, pp. 1269-1272 (Dec. 1998).

Zempleni, J. et al., "The utilization of intravenously infused pyridoxine in humans", *Clinica Chimica Acta*, vol. 229, Nos. 1, 2, pp. 27-36 (Sep. 1994).

Kuo & Wang, "Pyridoxal Phosphate-Responsive Epilepsy with Resistance to Pyridoxine," *Pediatric Neuro.*, 26(2):146-147 (2002).

Onorato, et al., "Pyridoxamine, an Inhibitor of Advanced Glycation Reactions, Also Inhibits Advanced Lipoxidation Reactions," *J. Biol. Chem.*, 275(28):21177-21184, Jul. 14, 2000.

Schaumburg, et al., "Sensory Neuropathy from Pyridoxine abuse," *N. Eng. J. Med.*, 309(8):445-448, Aug. 25, 1983.

Yamashima, et al., "Neuroprotective Effects of Pyridoxal Phosphate and Pyridoxal Against Ischemia in Monkeys," *Nutritional Neuroscience*, 4:389-397 (2001).

"Dietary Reference Intakes for Thiamin, Riboflavin, Niacin, Vitamin B6, Folate, Vitamin B12, Panthothenic Acid, Biotin, and Choline" A Report on the Standing Committee on the Scientific Evaluation of Dietary Reference Intakes and its Panel on Folate, Other B Vitamins, and Choline and Subcommittee on Upper Reference Levels of Nutrients, Food and Nutrition Board, Institute of Medicine (1998) (ISBN 0-309-06554-2).

Bässler, "Megavitamin Therapy with Pyridoxine", *Internat. J. Vit. Nutr. Res.* 58: 105-118 (1988).

BØnaa et al., "Homocysteine lowering and cardiovascular events after acute myocardial infarction", *N. Eng. J. Med.* 354: (2006); DO1:10.1056/NEJM01055227 (including supplementary appendix).

Chumnantana et al., "Vitamin B$_6$ compounds prevent the death of yeast cells due to menadione, a reactive oxygen generator", *Biochimica et Biophysica Acta* 1722:84-91 (2005).

Higuchi et al. "Aminophospholipid glycation and its inhibitor screening system: A new role of pyridoxal 5'-phosphate and pyridoxal as lipid glycation inhibitor", *J Lipid Res.* 2006 Feb 9; doi:10.1194/jlr.M500348-JLR200.

Hirai et al., "Cerebrospinal fluid somatostatin in West syndrome: changes in response to combined treatment with high-dose pyridoxal phosphate and low-dose cortiscotropin", *Neuropeptides*, 32(6):581-586 (1998).

Holman, "Pyridoxine—Vitmain B-6", *J. Austral. Coll. Nutr. Environ. Med.* 14: 5-16 (1995).

Kannan et al., "Effect of Vitamin B6 on oxygen radicals, mitochondrial memberane potential, and lipid peroxidation in H2O2-treated U937 monocytes", *Free Radical Biol. Med.* 36: 423-428 (2004).

Kolata, "Studies suggest B vitamins don't prevent heart attacks", *N.Y. Times*, Mar. 13, 2006 at p. 14, section A, col. 3.

Kuo et al. "Pyridoxal phosphate-responsive epilepsy with resistance to pyridoxine", *Pediatr. Neurol.* 26: 146-147 (2002).

Ohtsuka et al., "Treatment of the West Syndrome with High-Dose Pyridoxal Phosphate", *Brain & Development* 9(4):418-421 (1987).

Schaumberg et al., "Sensory neuropathy from pyridoxine abuse", *N. Eng. Med. J.* 309: 445-448 (1983).

Seki, "Combination Treatment of High-Dose Pyridoxal Phosphate and Low-Dose ACTH in Children with West Syndrome and Related Disorders", *The Japanese Journal of Psychiatry and Neurologyv* 44(2):219-237 (1990).

The Heart Outcomes Prevention Evaluation (HOPE) 2 Investigators, "Homocysteine lowering with folic acid and B vitamines in vascular disease" *N. Eng. J. Med.* 354: (2006); DOI:10.1056/NEJM060900 (including supplementary appendix).

Ubbink et al., "Effect of different levels of oral pyridoxine supplementation on plasma pyridoxal-5'-phosphate and pyridoxal levels and urinary vitamin B-6 excretion," *Am. J. Clin. Nutr.* 46: 78-85 (1987).

Wang et al., "Pyridoxal phosphate is better than pyridoxine for controlling idiopathic intractable epilepsy" *Arch. Dis. Child.* 90: 512-515 (2005).

Kok, F. et al., "Low Vitamin B$_₆$ Status in Patients with Acute Myocardial Infarction", *Am. J. Cardiol.*, vol. 63, pp. 513-516 (Mar. 1, 1989).

* cited by examiner

TREATMENT OF CARDIOVASCULAR AND RELATED PATHOLOGIES

This application claims priority to provisional application Serial No. 60/150,415 filed on Aug. 24, 1999. This application is a divisional of U.S. application Ser. No. 09/645,237, now U.S. Pat. No. 6,677,356, filed on Aug. 24, 2000.

FIELD OF THE INVENTION

This invention relates to methods of treating cardiovascular and related diseases, such as hypertrophy, hypertension, congestive heart failure, ischemia, such as myocardial ischemia, ischemia reperfusion injuries in various organs, arrhythmia, and myocardial infarction.

BACKGROUND

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure may ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic and/or diastolic blood pressures. Hypertension places increased tension to the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of its blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ affected is the heart, this condition is known as myocardial ischemia, and myocardial ischemia initially leads to abnormal electrical activity. This may generate an arrhythmia. When myocardial ischemia is of sufficient severity and duration, cell injury may progress to cell death—i.e., myocardial infarction—and subsequently to heart failure, hypertrophy, or congestive heart failure.

When blood flow resumes to an organ after temporary cessation, this is known as ischemic reperfusion of the organ. For example, reperfusion of an ischemic myocardium may counter the effects of coronary occlusion, a condition that leads to myocardial ischemia. Ischemic reperfusion to the myocardium may lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Drug therapies, using known active ingredients such as vasodilators, angiotensin II receptor antagonists, angiotensin converting enzyme inhibitors, diuretics, antithrombolytic agents, β-adrenergic receptor antagonists, α-adrenergic receptor antagonists, calcium channel blockers, and the like, are available for treating heart failure and associated diseases. Of course, any drug used for treatment may result in side effects. For example, vasodilators may result in hypotension, myocardial infarction, and adverse immune response. Angiotensin II receptor antagonists and angiotensin converting enzyme inhibitors are often associated with acute renal failure, fetopathic potential, proteinuria, hepatotoxicity, and glycosuria as side effects. Similarly, common side effects associated with calcium channel blockers include hypotension, peripheral edema, and pulmonary edema. β-Adrenergic receptor antagonists and diuretics have been associated with incompatibility with nonsteroidal anti-inflammatory drugs in addition to impotence, gout, and muscle cramps in the case of diuretics and in addition to a decrease in left ventricular function and sudden withdrawal syndrome in the case of β-adrenergic receptor antagonists. Moreover, side effects associated with α-adrenergic receptor antagonists include thostatic hypotension, and side effects associated with antithrombolytic agents include excessive bleeding.

To address the side effects, the dosage of a drug may be reduced or the administration of the drug may be abated and replaced with another drug. It would be desirable to administer a drug therapy with decreased amounts of the active ingredient to reduce side effects but maintain effectiveness.

SUMMARY OF THE INVENTION

The present invention provides methods for treating cardiovascular and related diseases, such as, for example, hypertrophy, hypertension, congestive heart failure, myocardial ischemia, ischemia reperfusion injuries in an organ, arrhythmia, and myocardial infarction. One embodiment is directed to a method of treating cardiovascular disease in a mammal by concurrently administering to the mammal a therapeutically effective amount of a combination of a compound suitable for use in methods of the invention and a therapeutic cardiovascular compound. Therapeutic cardiovascular compounds suitable for use in methods of the invention include an angiotensin converting enzyme inhibitor, an angiotensin II receptor antagonist, a calcium channel blocker, an antithrombolytic agent, a β-adrenergic receptor antagonist, a vasodilator, a diuretic, an α-adrenergic receptor antagonist, an antioxidant, and a mixture thereof. In some embodiments, the therapeutic cardiovascular compound is PPADS.

Compounds suitable for use in the methods of the invention include pyridoxal-5'-phosphate, pyridoxamine, pyridoxal, 3-acylated pyridoxal analogues, pharmaceutically acceptable acid addition salts thereof, and mixtures thereof.

In one embodiment, a 3-acylated pyridoxal analogue is a compound of the formula

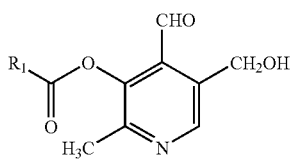

In another embodiment, a 3-acylated pyridoxal analogue is a compound of the formula

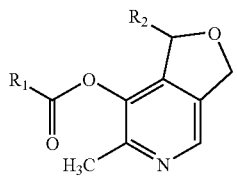

DESCRIPTION OF THE INVENTION

Figure 1:
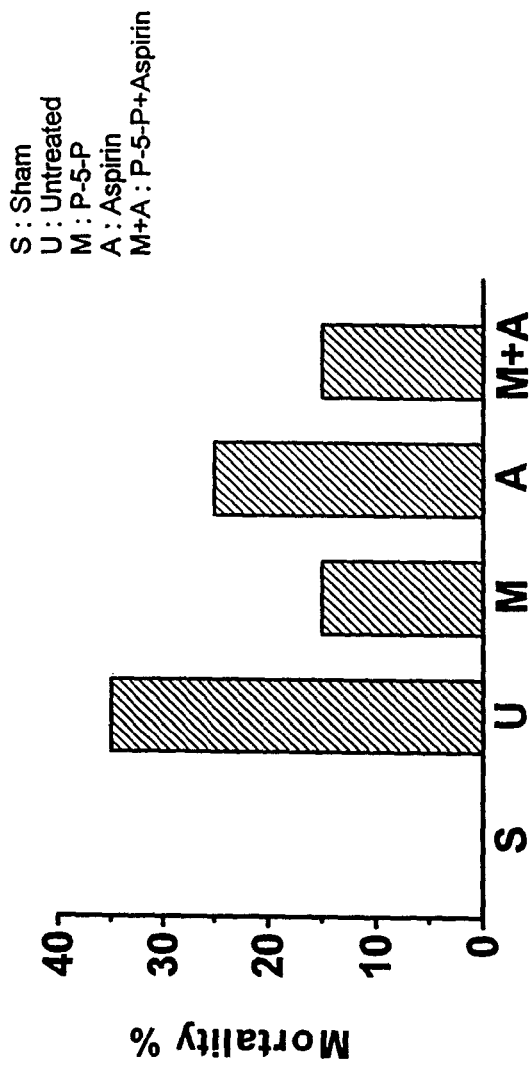
FIG. 1 is a graph showing the effect of P-5-P and aspirin, alone or in combination, on mortality in the rat model of coronary ligation.

The present invention provides methods for treatment of cardiovascular and related diseases or conditions. Such cardiovascular and related diseases include hypertrophy, hypertension, congestive heart failure, ischemia, such as myocardial ischemia, ischemia reperfusion injury, arrhythmia, and myocardial infarction.

In accordance with the present invention, it has been found that pyridoxal-5'-phosphate and its derivatives can be used concurrently with therapeutic cardiovascular compounds in the treatment of the above-identified diseases and conditions. "Treatment" and "treating" as used herein include preventing, inhibiting, and alleviating cardiovascular diseases, related diseases, and related symptoms as well as healing the ischemia-related conditions or symptoms thereof affecting mammalian organs and tissues. Treatment may be carried out by concurrently administering a therapeutically effective amount of a combination of a compound suitable for use in methods of the invention and a therapeutic cardiovascular compound.

A "therapeutically effective amount" as used herein includes a prophylactic amount, for example, an amount effective for preventing or protecting against cardiovascular diseases, related diseases, and symptoms thereof, and amounts effective for alleviating or healing cardiovascular diseases, related diseases, and symptoms thereof. By administering a compound suitable for use in methods of the invention concurrently with a therapeutic cardiovascular compound, the therapeutic cardiovascular compound may be administered in a dosage amount that is less than the dosage amount required when the therapeutic cardiovascular compound is administered as a sole active ingredient. By administering lower dosage amounts of the active ingredient, the side effects associated therewith should accordingly be reduced.

Compounds suitable for use in the methods of the invention include pyridoxal-5'-phosphate, pyridoxal, pyridoxamine, 3-acylated pyridoxal analogues, pharmaceutically acceptable acid addition salts thereof, and mixtures thereof. 3-Acylated pyridoxal analogues provide for slower metabolism to pyridoxal in vivo. For example, a suitable 3-acylated analogue of pyridoxal (2-methyl-3-hydroxy-4-formyl-5-hydroxymethylpyridine) is a compound of the formula I:

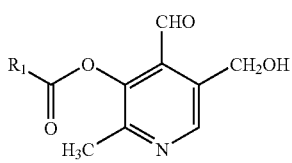

or a pharmaceutically acceptable acid addition salt thereof, wherein $R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group.

The term "alkyl" group includes a straight or branched saturated aliphatic hydrocarbon chain having from 1 to 8 carbon atoms, such as, for example, methyl, ethyl, propyl, isopropyl (1-methylethyl), butyl, tert-butyl (1,1-dimethylethyl), and the like.

The term "alkenyl" group includes an unsaturated aliphatic hydrocarbon chain having from 2 to 8 carbon atoms, such as, for example, ethenyl, 1-propenyl, 2-propenyl, 1-butenyl, 2-methyl-1-propenyl, and the like.

The above alkyl or alkenyl groups may optionally be interrupted in the chain by a heteroatom, such as, for example, a nitrogen or oxygen atom, forming an alkylaminoalkyl or alkoxyalkyl group, for example, methylaminoethyl or methoxymethyl, and the like.

The term "alkoxy" group includes an alkyl group as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The term "dialkylamino" group includes two alkyl groups as defined above joined to a nitrogen atom, in which the alkyl group has preferably 1 to 4 carbon atoms, such as, for example, dimethylamino, diethylamino, methylethylamino, methylpropylamino, diethylamino, and the like.

The term "aryl" group includes an aromatic hydrocarbon group, including fused aromatic rings, such as, for example, phenyl and naphthyl. Such groups may be unsubstituted or substituted on the aromatic ring by, for example, an alkyl group of 1 to 4 carbon atoms, an alkoxy group of 1 to 4 carbon atoms, an amino group, a hydroxy group, or an acetyloxy group.

Preferred $R_1$ groups for compounds of formula I are toluyl or naphthyl. Such $R_1$ groups when joined with a carbonyl group form an acyl group

which preferred for compounds of formula I include toluoyl or β-naphthoyl. Of the toluoyl group, the p-isomer is more preferred.

Examples of 3-acylated analogues of pyridoxal include, but are not limited to, 2-methyl-3-toluoyloxy-4-formyl-5-hydroxymethylpyridine and 2-methyl-β-naphthoyloxy-4-formyl-5-hydroxymethylpyridine.

Another suitable analogue is a 3-acylated analogue of pyridoxal-4,5-aminal (1-secondary amino-1,3-dihydro-7-hydroxy-6-methylfuro(3,4-c)pyridine) of the formula II:

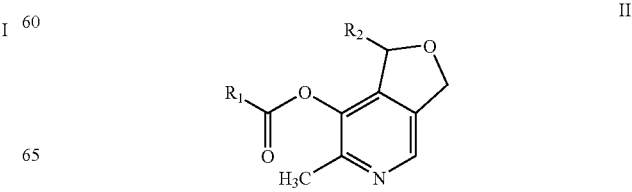

or a pharmaceutically acceptable acid addition salt thereof, wherein

R$_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group; and R$_2$ is a secondary amino group.

The terms "alkyl," "alkenyl," "alkoxy," "dialkylamino," and "aryl" are as defined above.

The term "secondary amino" group includes a group of the formula III:

III derived from a secondary amine R$_3$R$_4$NH, in which R$_3$ and R$_4$ are each independently alkyl, alkenyl, cycloalkyl, aryl, or, when R$_3$ and R$_4$ are taken together, may form a ring with the nitrogen atom and which may optionally be interrupted by a heteroatom, such as, for example, a nitrogen or oxygen atom. The terms "alkyl," "alkenyl," and "aryl" are used as defined above in forming secondary amino groups such as, for example, dimethylamino, methylethylamino, diethylamino, dialkylamino, phenylmethylamino, diphenylamino, and the like.

The term "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

When R$_3$ and R$_4$ are taken together with the nitrogen atom, they may form a cyclic secondary amino group, such as, for example, piperidino, and, when interrupted with a heteroatom, includes, for example, piperazino and morpholino.

Preferred R$_1$ groups for compounds of formula II include toluyl, e.g., p-toluyl, naphthyl, tert-butyl, dimethylamino, acetylphenyl, hydroxyphenyl, or alkoxy, e.g., methoxy. Such R$_1$ groups when joined with a carbonyl group form an acyl group

which preferred for compounds of formula II include toluoyl, β-naphthoyl, pivaloyl, dimethylcarbamoyl, acetylsalicyloyl, salicyloyl, or alkoxycarbonyl. A preferred secondary amino group may be morpholino.

Examples of 3-acylated analogues of pyridoxal-4,5-aminal include, but are not limited to, 1-morpholino-1,3-dihydro-7-(p-toluoyloxy)-6-methylfuro(3,4-c)pyridine; 1-morpholino-1,3-dihydro-7-(β-naphthoyloxy)-6-methylfuro(3,4-c)pyridine; 1-morpholino-1,3-dihydro-7-pivaloyloxy-6-methylfuro(3,4-c)pyridine; 1-morpholino-1,3-dihydro-7-carbamoyloxy-6-methylfuro(3,4-c)pyridine; and 1-morpholino-1,3-dihydro-7-acetylsalicyloxy-6-methylfuro(3,4-c)pyridine.

The compounds of formula I may be prepared by reacting pyridoxal hydrochloride with an acyl halide in an aprotic solvent. A suitable acyl group is

wherein R$_1$ is as defined above. A particularly suitable acyl halide includes p-toluoyl chloride or β-naphthoyl chloride. A suitable aprotic solvent includes acetone, methylethylketone, and the like.

The compounds of formula II may be prepared by reacting 1-secondary amino-1,3-dihydro-7-hydroxy-6-methylfuro(3,4-c)pyridine with an acyl halide in an aprotic solvent. An acyl group is

wherein R$_1$ is as defined above. A particularly suitable acyl halide includes p-toluoyl chloride, β-naphthoyl chloride, trimethylacetyl chloride, dimethylcarbamoyl chloride, and acetylsalicyloyl chloride. A particularly suitable secondary amino group includes morpholino.

The compound 1-morpholino-1,3-dihydro-7-hydroxy-6-methylfuro(3,4-c)pyridine may be prepared by methods known in the art, for example, by reacting morpholine and pyridoxal hydrochloride at a temperature of about 100° C. in a solvent. A suitable solvent includes, for example, toluene. Similarly, other secondary amines as defined for R$_2$ may be used as reactants to prepare the appropriate 1-secondary amino compounds.

The compounds of formula I may alternatively be prepared from the compounds of formula II by reacting a compound of formula II with an aqueous acid, such as, for example, aqueous acetic acid.

One skilled in the art would recognize variations in the sequence and would recognize variations in the appropriate reaction conditions from the analogous reactions shown or otherwise known that may be appropriately used in the above-described processes to make the compounds of formulas I and II herein.

The products of the reactions described herein are isolated by conventional means such as extraction, distillation, chromatography, and the like.

Pharmaceutically acceptable acid addition salts of compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate N-methyl glutamine, etc., as disclosed for example by Berge et al. in their publication entitled Pharmaceutical Salts, in *J Pharmaceutical Science*, 66: 1–19 (1977). Berge et al. outlined various potential useful salts along with their physicochemical studies, their bioavailabilities, their pharmacological studies and their toxicologies.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Methods of the invention include concurrently administering pyridoxal-5'-phosphate, pyridoxamine, pyridoxal, a 3-acylated pyridoxal analogue, a pharmaceutically acceptable acid addition salt thereof, or a mixture thereof with a therapeutic cardiovascular compound to treat hypertrophy, hypertension, congestive heart failure, ischemia, such as myocardial ischemia, ischemia reperfusion injury, arrhythmia, or myocardial infarction. Preferably, the cardiovascular disease treated is hypertrophy or congestive heart failure. Still preferably, the cardiovascular disease treated is arrhythmia. Also preferably, the cardiovascular disease treated is ischemia reperfusion injury.

Therapeutic cardiovascular compounds that may be concurrently administered with a compound suitable for use in methods of the invention include an angiotensin converting enzyme inhibitor, an angiotensin II receptor antagonist, a calcium channel blocker, an antithrombolytic agent, a β-adrenergic receptor antagonist, a vasodilator, a diuretic, an α-adrenergic receptor antagonist, an antioxidant, and a mixture thereof. A compound suitable for use in methods of the invention also may be concurrently administered with PPADS (pyridoxal phosphate-6-azophenyl-2',4'-disulphonic acid), also a therapeutic cardiovascular compound, or with PPADS and another known therapeutic cardiovascular compound as already described. In a preferred embodiment, pyridoxal-5'-phosphate is concurrently administered with PPADS or with PPADS and another known therapeutic cardiovascular compound, preferably an angiotensin converting enzyme inhibitor or an angiotensin II receptor antagonist.

Preferably, a therapeutic cardiovascular compound, which is concurrently administered with pyridoxal-5'-phosphate, pyridoxamine, pyridoxal, a 3-acylated pyridoxal analogue, a pharmaceutically acceptable acid addition salt thereof, or a mixture thereof, is an angiotensin converting enzyme inhibitor, an angiotensin II receptor antagonist, or a diuretic. Still preferably, the therapeutic cardiovascular compound is an α-adrenergic receptor antagonist. Also preferably, the therapeutic cardiovascular compound is a calcium channel blocker.

These therapeutic cardiovascular compounds are generally used to treat cardiovascular and related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia may be treated by the administration of, for example, angiotensin converting enzyme inhibitor, an angiotensin II receptor antagonist, a calcium channel blocker, an antithrombolytic agent, a β-adrenergic receptor antagonist, a diuretic, an α-adrenergic receptor antagonist, or a mixture thereof. In some instances, congestive heart failure may be treated by the administration of, for example, angiotensin converting enzyme inhibitor, an angiotensin II receptor antagonist, a calcium channel blocker, a vasodilator, a diuretic, or a mixture thereof.

Myocardial infarction may be treated by the administration of, for example, angiotensin converting enzyme inhibitor, a calcium channel blocker, an antithrombolytic agent, a β-adrenergic receptor antagonist, a diuretic, an α-adrenergic receptor antagonist, or a mixture thereof.

Hypertension may be treated by the administration of, for example, angiotensin converting enzyme inhibitor, a calcium channel blocker, a β-adrenergic receptor antagonist, a vasodilator, a diuretic, an α-adrenergic receptor antagonist, or a mixture thereof.

Moreover, arrhythmia may be treated by the administration of, for example, a calcium channel blocker, a β-adrenergic receptor antagonist, or a mixture thereof.

Antithrombolytic agents are used for reducing or removing blood clots from arteries.

Hypertropy may be treated by the administration of, for example, an angiotensin converting enzyme inhibitor, an angiotensin II receptor antagonist, a calcium channel blocker, or a mixture thereof.

Ischemia reperfusion injury may be treated by the administration of, for example, an angiotensin converting enzyme inhibitor, an angiotensin II receptor antagonist, a calcium channel blocker, or a mixture thereof.

Known angiotensin converting enzyme inhibitors include, for example, captopril, enalapril, lisinopril, benazapril, fosinopril, quinapril, ramipril, spirapril, imidapril, and moexipril.

Examples of known angiotensin II receptor antagonists include both angiotensin I receptor subtype antagonists and angiotensin II receptor subtype antagonists. Suitable angiotensin II receptor antagonists include losartan and valsartan.

Suitable calcium channel blockers include, for example, verapamil, diltiazem, nicardipine, nifedipine, amlodipine, felodipine, nimodipine, and bepridil.

Antithrombolytic agents known in the art include antiplatelet agents, aspirin, and heparin.

Examples of known β-adrenergic receptor antagonists include atenolol, propranolol, timolol, and metoprolol.

Suitable vasodilators include, for example, hydralazine, nitroglycerin, and isosorbide dinitrate.

Suitable diuretics include, for example, furosemide, diuril, amiloride, and hydrodiuril.

Suitable α-adrenergic receptor antagonists include, for example, prazosin, doxazocin, and labetalol.

Suitable antioxidants include vitamin E, vitamin C, and isoflavones.

A compound suitable for use in methods of the invention and a therapeutic cardiovascular compound are administered concurrently. "Concurrent administration" and "concurrently administering" as used herein includes administering a compound suitable for use in methods of the invention and a therapeutic cardiovascular compound in admixture, such as, for example, in a pharmaceutical composition or in solution, or as separate compounds, such as, for example, separate pharmaceutical compositions or solutions administered consecutively, simultaneously, or at different times but not so distant in time such that the compound suitable for use in methods of the invention and the therapeutic cardiovascular compound cannot interact and a lower dosage amount of the active ingredient cannot be administered.

A physician or veterinarian of ordinary skill readily determines a subject who is exhibiting symptoms of any one or more of the diseases described above. Regardless of the route of administration selected, the compound suitable for use in methods of the invention and the therapeutic cardiovascular compound are formulated into pharmaceutically acceptable unit dosage forms by conventional methods known to the pharmaceutical art. An effective but nontoxic quantity of the compound suitable for use in methods of the invention and the therapeutic cardiovascular compound are employed in the treatment.

The compound suitable for use in methods of the invention and the therapeutic cardiovascular compound may be concurrently administered enterally and/or parenterally in admixture or separately. Parenteral administration includes subcutaneous, intramuscular, intradermal, intramammary, intravenous, and other administrative methods known in the art. Enteral administration includes tablets, sustained release tablets, enteric coated tablets, capsules, sustained release capsules, enteric coated capsules, pills, powders, granules, solutions, and the like.

A pharmaceutical composition suitable for administration comprises a pharmaceutically acceptable carrier and a compound suitable for use in methods of the invention and/or a therapeutic cardiovascular compound. The pharmaceutical composition comprises a pharmaceutically acceptable carrier and a compound suitable for use in methods of the invention, such as, for example, pyridoxal-5'-phosphate, pyridoxal, pyridoxamine, a 3-acylated pyridoxal analogue, a pharmaceutically acceptable acid addition salt thereof, and a mixture thereof. A pharmaceutically acceptable carrier includes, but is not limited to, physiological saline, ringers, phosphate buffered saline, and other carriers known in the art. Pharmaceutical compositions may also include stabilizers, antioxidants, colorants, and diluents. Pharmaceutically acceptable carriers and additives are chosen such that side effects from the pharmaceutical compound are reduced or minimized and the performance of the compound is not canceled or inhibited to such an extent that treatment is ineffective.

Methods of preparing pharmaceutical compositions containing a pharmaceutically acceptable carrier and a compound suitable for use in methods of the invention and/or a therapeutic cardiovascular compound are known to those of skill in the art. All methods may include the step of bringing the compound suitable for use in methods of the invention and/or the therapeutic cardiovascular compound in association with the carrier or additives. In general, the formulations are prepared by uniformly and intimately bringing the compound into association with a liquid carrier or a finely divided solid carrier or both, and then, if necessary, shaping the product into the desired unit dosage form.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutically effective amount of a compound suitable for use in methods of the invention to treat cardiovascular and related diseases as well as symptoms thereof is typically in a range of about 0.1–100 mg/kg of a patient's body weight, more preferably in the range of about 0.5–50 mg/kg of a patient's body weight per daily dose when administered alone. The compound suitable for use in methods of the invention may be administered for periods of short and long duration.

Therapeutically effective amounts of respective therapeutic cardiovascular compounds when administered as sole active ingredients are known in the art and may be found in, for example, *Physicians' Desk Reference* ($53^{rd}$ ed., 1999).

When concurrently administering a compound suitable for use in methods of the invention and a therapeutic cardiovascular compound, the compound suitable for use in methods of the invention is typically administered in a range of about 0.1–100 mg/kg of a patient's body weight, preferably 0.5–50 mg/kg of a patient's body weight, per daily dose, and the therapeutic cardiovascular compound is administered in an amount less than the amount known in the art, which is administered when the therapeutic cardiovascular compound is administered as the sole active ingredient. Typically, the therapeutic cardiovascular compound is administered in an amount at least 5% less than the amount known in the art, which is administered when the therapeutic cardiovascular compound is administered as the sole active ingredient.

A therapeutically effective amount of a compound suitable for use in methods of the invention and a therapeutic cardiovascular compound for treating cardiovascular and related diseases and symptoms thereof can be administered prior to, concurrently with, or after the onset of the disease or symptom. For example, a therapeutically effective amount of a compound suitable for use in methods of the invention and a therapeutic cardiovascular compound for treating ischemia reperfusion injury or myocardial infarction can be administered before, during, or following ischemia (including during or following reperfusion), as well as continually for some period spanning from pre- to post-ischemia. For example, the compound suitable for use in methods of the invention and a therapeutic cardiovascular compound may be concurrently administered prior to heart procedures, including bypass surgery, thrombolysis, and angioplasty, and prior to any other procedures that require blood flow be interrupted and then resumed. Additionally, a compound suitable for use in methods of the invention and a therapeutic cardiovascular compound may be taken on a regular basis to protect against cellular dysfunction arising from arrhythmia and heart failure.

The invention is further elaborated by the representative examples as follows. Such examples are not meant to be limiting.

EXAMPLES

Example 1

Synthesis of morpholine pyridoxal-4,5-aminal (1-morpholino-1,3-dihydro-7-hydroxy-6-methylfuro (3,4-c)pyridine)

A mixture of morpholine (20 g) and toluene (100 mL) was stirred and heated using an oil bath set to 100° C. for 15 minutes. Pyridoxal hydrochloride (10 g) was then added and the reaction mixture was stirred at 100° C. for two hours. The reaction mixture was then concentrated by distillation of the toluene and morpholine. The concentrated reaction mixture was washed three times by adding toluene (100 mL) and removing the toluene by distillation. After washing, the residue was dissolved in toluene and filtered, and then hexane was added until precipitation began, at which time the reaction mixture was left overnight at room temperature. Crystals were collected and washed thoroughly with hexane.

Nuclear magnetic resonance spectroscopy (NMR) and mass spectroscopy confirmed the identity of the synthesized compound. The purity of the compound was analyzed by high performance liquid chromatography (HPLC) using a C-18 reverse phase column and water/acetonitrile as solvent (1–100% acetonitrile over 25 minutes).

Example 2

Synthesis of the 3-toluate of the morpholine pyridoxal-4.5-aminal (1-morpholino-1,3-dihydro-7-(p-toluoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The reaction mixture was cooled to between 0 and 5° C. and then p-toluoyl chloride (1.06 g, 6 mmoles) in acetone (20 mL) was added. This mixture was stirred for two hours, followed by filtering out the solid and evaporating the solution to dryness under vacuum. The residue was chromatographed on silica gel using a mixture of ethyl acetate and hexane as solvent.

The purified solid was analyzed by thin layer chromatography (TLC), NMR, and mass spectroscopy. The purity of the synthesized compound was confirmed by HPLC as described in Example 1.

Example 3

Synthesis of the 3-toluate of pyridoxal (2-methyl-3-toluoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and thenp-toluoyl chloride (2.12 g, 12 mmoles) in acetone (20 mL) was added. The reaction mixture was stirred for two hours followed by filtering out the solid and evaporating the solution to dryness under vacuum. The residue was chromatographed on silica gel as described in Example 2.

The purified solid was analyzed by TLC, NMR, and mass spectroscopy. The purity of the compound was confirmed by HPLC as described in Example 1.

Alternative to the above-described method, the 3-toluate of pyridoxal is synthesized by reacting the compound of Example 2 with 80% aqueous acetic acid at 60° C. for 30 minutes, and then diluting with water and extracting by ethyl acetate. The ethyl acetate layer is washed with 5% aqueous sodium bicarbonate, dried with magnesium sulfate, and evaporated to dryness. The compound is also analyzed as described supra.

Example 4

Synthesis of 3-β-naphthoate of the morpholine pyridoxal-4,5-aminal (1-morpholino-1,3-dihydro-7-(β-naphthoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The mixture was cooled to between 0 and 5° C. and then β-naphthoyl chloride (1.06 g, 6 mmoles) in acetone (20 mL) was added. The reaction mixture was stirred for two hours, and then the solid was filtered out and the solution was evaporated to dryness under vacuum. The residue was chromatographed according to Example 2.

The purified solid was analyzed according to Example 2, and the purity was confirmed according to Example 1.

Example 5

Synthesis of the 3-β-naphthoate of pyridoxal (2-methyl-3-β-naphthoyloxy-4-formyl-5-hydroxymethylpyidine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then β-naphthoyl chloride (2.12 g, 12 mmoles) in acetone (20 mL) was added and the mixture was stirred for two hours. The solid was filtered out and the solution was evaporated to dryness under vacuum. The residue was chromatographed according to Example 2.

The purified solid was analyzed according to Example 2, and the purity was confirmed according to Example 1.

Alternative to the above-described synthesis, the 3-β-naphthoate of pyridoxal is prepared by reacting the compound of Example 4 with 80% aqueous acetic acid at 60° C. for 30 minutes, followed by diluting with water and extracting by ethyl acetate. The ethyl acetate layer is then washed with 5% aqueous sodium bicarbonate, dried with magnesium sulfate, and evaporated to dryness. The compound is also analyzed as described supra.

Example 6

Synthesis of 3-pivaloyl of the morpholine pyridoxal-4,5-aminal (1-morpholino-1,3-dihydro-7-pivaloyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The mixture was cooled to between 0 and 5° C. and then pivaloyl chloride (trimethylacetyl chloride) (720 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

Example 7

Synthesis of 3-dimethylcarbamoyl of the morpholine pyridoxal-4,5-aminal (1-morpholino-1,3-dihydro-7-(dimethylcarbamovloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The mixture was cooled to between 0 and 5° C. and then dimethylcarbamoyl chloride (642 mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

Example 8

Synthesis of 3-acetylsalicyloyl of the morpholine pyridoxal-4,5-aminal (1-morpholino-1,3-dihydro-7-acetylsalicyloxy-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The mixture was cooled to between 0 and 5° C. and then acetylsalicyloyl chloride (1.09 g, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

Example 9

In Vitro—Ischemia Reperfusion in Isolated Rat Hearts and Measurement of Left Ventricular Developed Pressure (LVDP)

Male Sprague-Dawley rats weighing 250–300 g are anaesthetized with a mixture of ketamine (60 mg/kg) and xylazine (10 mg/kg). The hearts are rapidly excised, cannulated to a Langendorff apparatus and perfused with Krebs-Henseleit-solution, gassed with a mixture of 95% $O_2$ and 5% $CO_2$, pH 7.4. The perfusate contained (in mM): 120 NaCl, 25 $NaHCO_3$, 11 glucose, 4.7 KCl, 1.2 $KH_2PO_4$, 1.2 $MgSO_4$4 and 1.25 $CaCl_2$.

The hearts are electrically stimulated at a rate of 300 beats/min (Phipps and Bird Inc., Richmond, Va.) and a water-filled latex balloon is inserted in the left ventricle and connected to a pressure transducer (Model 1050BP; BYO-PAC SYSTEM NC., Goleta, Calif.) for the left ventricular systolic measurements. The left ventricular end diastolic pressure (LVEDP) is adjusted at 10 mmHg at the beginning of the experiment. In some experiments the left ventricular pressures are differentiated to estimate the rate of ventricular contraction (+dP/dt) and rate of ventricular relaxation (−dP/dt) using the Acknowledge 3.03 software for Windows (BIOPAC SYSTEM INC.,) Goleta, Calif.). All hearts are stabilized for a period of 30 min and then randomly distributed into nine different experimental groups (n=5–8 per group). The experimental groups are defined as follows:

1) Control group (control hearts are further perfused for 90 minutes for a total of 130 min of continuous perfusion);
2) Ischemia reperfusion group (Ischemia reperfusion hearts are made globally ischemic by stopping the coronary flow completely for 30 min and then the hearts are reperfused for 60 min);
3) P-5-P (15 µM) treated group;
4) captopril (100 µM) treated group;
5) verapamil (0.01 µM) ) treated group;
6) propranolol ( 3 mM) treated group;
7) PPADS (10 µM) treated group;
8) P-5-P+captopril treated group;
9) P-5-P+verapamil treated group;
10) P-5-P+propranolol treated group;
11) P-5+P PPADS treated group.

Drug treatment is started 10 min before global ischemia followed by 30 min global ischemia and 60 min reperfusion. At the end of some experiments, the hearts are quickly freeze-clamped with a liquid nitrogen precooled Wollenberger tong. Rats are housed in clear cages in a temperature and humidity controlled room on a 12 hr light-dark cycle. Food and water are supplied ad libitum.

Hearts subject to 30 min of ischemia followed by 60 min of reperfusion showed slight recovery in the contractile function as represented by 29.5% recovery in LVDP (left ventricular developed pressure). As compared to the untreated group, treatment with P-5-P, captopril, or P-5-P and captopril showed better recoveries in LVDP by 78.2%, 61.4%, and 132% respectively (Table I).

TABLE I

Effect of Pyridoxal-5-phosphate (P-5-P, 15 µM) and Captopril (100 µM) on % recovery of left ventricular systolic pressure (LVDP).

| Drugs | LVDP (B) | LVDP (A) | LVEDP mmHg | LVSP mmHg | % recovery (LVDP) |
|---|---|---|---|---|---|
| Unreated | 87 ± 7 | 25 ± 2.9 | 62 ± 5.6 | 87 ± 6.9 | 29.5 ± 3.7 |
| P5P | 80 ± 3.8 | 63 ± 5 | 35 ± 4.8 | 98 ± 8.2 | 78.2 ± 3.3* |
| Captopril | 78 ± 10.9 | 47 ± 8.6 | 54 ± 6.7 | 101 ± 14.6 | 61.4 ± 5.2* |
| P5P + Captopril | 89 ± 6.9 | 69 ± 7.4 | 28 ± 7.3 | 117 ± 8.4 | 132 ± 7.5# |

(A) = After ischemia,
(B) = Before ischemia.

Hearts subject to 30 mm of ischemia followed by 60 min of reperfusion showed slight recovery in the contractile function as represented by 29.5% recovery in LVDP. As compared to the untreated group, treatment with P-5-P, verapamil, or P-5-P and verapamil showed better recoveries in LVDP by 78.2%, 43%, and 109% respectively (Table II).

TABLE II

Effect of Pyridoxal-5-phosphate (P-5-P, 15 μM) and Verapamil
(0.01 μM) on % recovery of left ventricular systolic pressure (LVDP).

|  | LVDP | | LVEDP | LVSP | % recovery |
|---|---|---|---|---|---|
| Drugs | (B) | (A) | mmHg | mmHg | (LVDP) |
| Untreated | 87 ± 7 | 25 ± 2.9 | 62 ± 5.6 | 87 ± 6.9 | 29.5 ± 3.7 |
| P5P | 80 ± 3.8 | 63 ± 5 | 35 ± 4.8 | 98 ± 8.2 | 78.2 ± 3.3* |
| Verapamil | 54 ± 9.1 | 23 ± 4.5 | 55 ± 5.1 | 78 ± 7.7 | 43 ± 6.6 |
| P5P + Verapamil | 78 ± 10.5 | 85 ± 11.7 | 34 ± 7.3 | 119 ± 8 | 109 ± 4.6# |

(A) = After ischemia,
(B) = Before ischemia.

Hearts subject to 30 min of ischemia followed by 60 min of reperfusion showed slight recovery in the contractile function as represented by 29.5% recovery in LVDP. As compared to the untreated group, treatment with P-5-P, PPADS, or P-5-P and PPADS showed better recoveries in LVDP by 78.2%, 61%, and 128% respectively (Table III).

TABLE III

Effect of Pyridoxal-5-phosphate (P-5-P, 15 μM) and Pyridoxal
phosphate 6-azophenyl-2'-4'disulfonic acid (PPADS 100 μM)
on % recovery of left ventricular systolic pressure (LVDP).

|  | LVDP | | LVEDP | LVSP | % recovery |
|---|---|---|---|---|---|
| Drugs | (B) | (A) | mmHg | mmHg | (LVDP) |
| Untreated | 87 ± 7 | 25 ± 2.9 | 62 ± 5.6 | 87 ± 6.9 | 29.5 ± 3.7 |
| P5P | 80 ± 3.8 | 63 ± 5 | 35 ± 4.8 | 98 ± 8.2 | 78.2 ± 3.3 |
| PPADS | 92 ± 15.2 | 58 ± 13.6 | 57 ± 6.3 | 115 ± 11.5 | 61 ± 4.8* |
| P5P + PPADS | 82 ± 15.8 | 105 ± 22.8 | 34 ± 3.1 | 139 ± 21.6 | 128 ± 13.8# |

(A) = After ischemia,
(B) = Before isehemia.

Hearts subject to 30 min of ischemia followed by 60 min of reperfusion showed slight recovery in the contractile function as represented by 29.5% recovery in LVDP. As compared to the untreated group, treatment with P-5-P, propranolol, or P-5-P and propranolol showed better recoveries in LVDP by 78.2%, 74%, and 120% respectively (Table IV).

Tables I–IV demonstrate that P-5-P in addition to providing significant benefit in ischemia reperfusion injury when given alone also improves or adds to the benefits associated with other commonly used drugs when given in combination with these drugs.

In addition to captopril, other angiotensin converting enzyme inhibitors, such as, for example, enalapril or imidapril, can similarly be administered in place of captopril. In addition to verapamil, other known calcium channel blockers, such as, for example, nifedipine or diltiazem, can similarly be administered in place of verapamil. In addition to propranolol, other β-adrenergic receptor antagonists such as, for example, atenolol, timolol, and metoprolol can similarly be administered in place of propranolol. Additionally,

TABLE IV

Effect of Pyridoxal-5-phosphate (P-5-P, 15 μM) and Propranolol
(3 μM) on % recovery of left ventricular systolic pressure (LVDP).

|  | LVDP | | LVEDP | LVSP | % recovery |
|---|---|---|---|---|---|
| Drugs | (B) | (A) | mmHg | mmHg | (LVDP) |
| Untreated | 87 ± 7 | 25 ± 2.9 | 62 ± 5.6 | 87 ± 6.9 | 29.5 ± 3.7 |
| P5P | 80 ± 3.8 | 63 ± 5 | 35 ± 4.8 | 98 ± 8.2 | 78.2 ± 3.3* |
| Propranolol | 61 ± 10.8 | 45 ± 9.7 | 27 ± 6.6 | 72 ± 15.1 | 74 ± 4.9* |
| P5P + Propranolol | 67 ± 12.6 | 75 ± 10.4 | 40 ± 4.2 | 115 ± 8.3 | 120 ± 15.5# |

(A) = After isehemia,
(B) = Before ischemia angiotensin II receptor antagonists such as, for example, losartan and valsartan can be used in the above example.

Example 10

In Vivo—Coronary Artery Ligation

Myocardial infarction is produced in male Sprague-Dawley rats (200–250 g) by occlusion of the left coronary artery as described in Sethi et al., *J. Cardiac Failure*, 1(5) (1995) and Sethi et al., *Am. J. Physiol.*, 272 (1997). The animals were anesthetized with ether, the skin incised along the left sternal border, the fourth rib cut proximal to the sternum, and retractors inserted. The pericardial sac was perforated and the heart was exteriorized through the intercostal space. The left coronary artery was ligated about 2 mm from its origin with a 6-0 silk suture and the heart was repositioned in the chest. Throughout the course of the operation, the rats were maintained on a positive pressure ventilation delivering a mixture of 95% $O_2$ and 5% $CO_2$ mixed with ether.

Rats are anesthetized with 1–5% isoflurane in 100% $O_2$ (2L flow rate). The skin is incised along the left sterna border and the 4th rib is cut proximal to the sternum and a retractor inserted. The pericardial sac is opened and the heart externalized. The left anterior descending coronary artery is ligated approximately 2 mm from its origin on the aorta using a 6-0 silk suture. The heart is then repositioned in the chest and the incision closed via purse-string sutures.

Sham operated rats undergo identical treatment except that the artery is not ligated. Mortality due to surgery is less than 1%. Unless indicated in the text, the experimental animals showing infarct size >30% of the left ventricle are used in this study. All animals are allowed to recover, allowed to receive food and water ad libitum, and are maintained for a period of 21 days for Electrocardiogram (ECG), hemodynamic, and histological assessment.

Occlusion of the coronary artery in rats has been shown to produce myocardial cell damage which results in scar formation in the left ventricle and heart dysfunction. While the complete healing of the scar occurs within 3 weeks of the coronary occlusion, mild, moderate and severe stages of congestive heart failure have been reported to occur at 4, 8 and 16 weeks after ligation. Accordingly, the contractile dysfunction seen at 3 weeks after the coronary occlusion in rats is due to acute ischemic changes.

The rats are housed in clear cages in a temperature and humidity controlled room, on a 12 hour light-dark cycle. Food and water are supplied ad libitum. After surgery, rats are randomly assigned to treatment or non-treatment in both sham and experimental groups. Randomization of animals was performed and treatment begins 1 hour after coronary occlusion and continues for 21 days. The total duration of experiments in each case is 21 days. The groups are as follows:

1) sham operated;
2) coronary artery ligated (treatment with equal volumes of saline);
3) coronary artery ligated (treated with 10 mg/kg P-5-P);
4) coronary artery ligated (treated with 100 mg/kg captopril);
5) coronary artery ligated (treated with 50 mg/kg propranolol);
6) coronary artery ligated (treated with 100 mg/kg aspirin);
7) coronary artery ligated (treated with 25 mg/kg verapamil);
8) coronary artery ligated (treated with 10 mg/kg P-5-P+100 mg/kg captopril);
9) coronary artery ligated (treated with 10 mg/kg P-5-P+50 mg/kg propranolol);
10) coronary artery ligated (treated with 10 mg/kg P-5-P+ 100 mg/kg aspirin);
11) coronary artery ligated (treated with 10 mg/kg P-5-P+25 mg/kg verapamil).

P-5-P (10 mg/kg), captopril (100 mg/kg), propranolol (50 mg/kg), verapamil (25 mg/kg) and aspirin (100 mg/kg) were administered once daily by gastric tube.

Acute myocardial infarction resulted in a total mortality of 35% % in the untreated group of rats in 21 days. The highest mortality occurred within the first 2 days following occlusion. As compared to the untreated group, treatment with P-5-P, aspirin, or P-5-P and aspirin showed lower mortality rates of 15%, 25%, 15%, respectively (FIG. 1).

Figure 2:
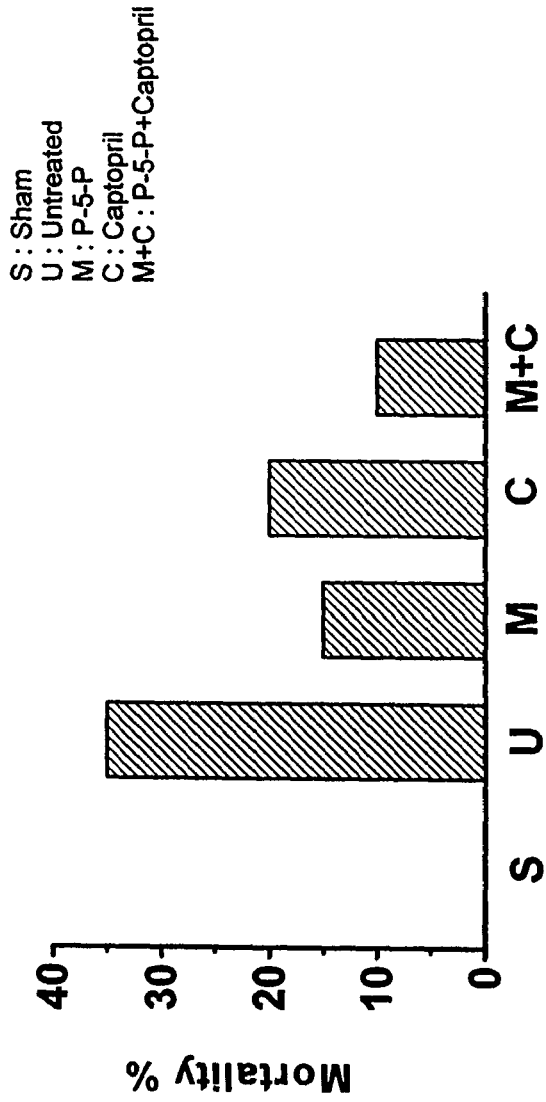
FIG. 2 is a graph showing the effect of P-5-P and captopril, alone or in combination, on mortality in the rat model of coronary ligation.

Acute myocardial infarction resulted in a total mortality of 35% % in the untreated group of rats in 21 days. The highest mortality occurred within the first 2 days following occlusion. As compared to the untreated group, treatment with P-5-P, captopril, or P-5-P and captopril showed lower mortality rates of 10%, 15%, 20%, respectively (FIG. 2).

Figure 3:
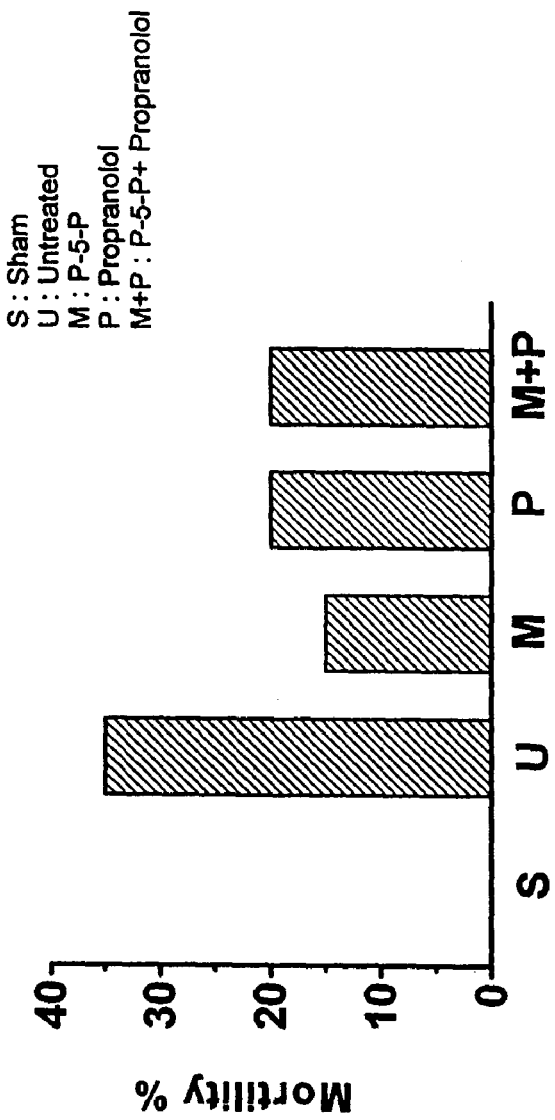
FIG. 3 is a graph showing the effect of P-5-P and propranolol, alone or in combination, on mortality in the rat model of coronary ligation.

Acute myocardial infarction resulted in a total mortality of 35% % in the untreated group of rats in 21 days. The highest mortality occurred within the first 2 days following occlusion. As compared to the untreated group, treatment with P-5-P, propranolol, or P-5-P and propranolol showed lower mortality rates of 15%, 20%, 20%, respectively (FIG. 3).

Figure 4:
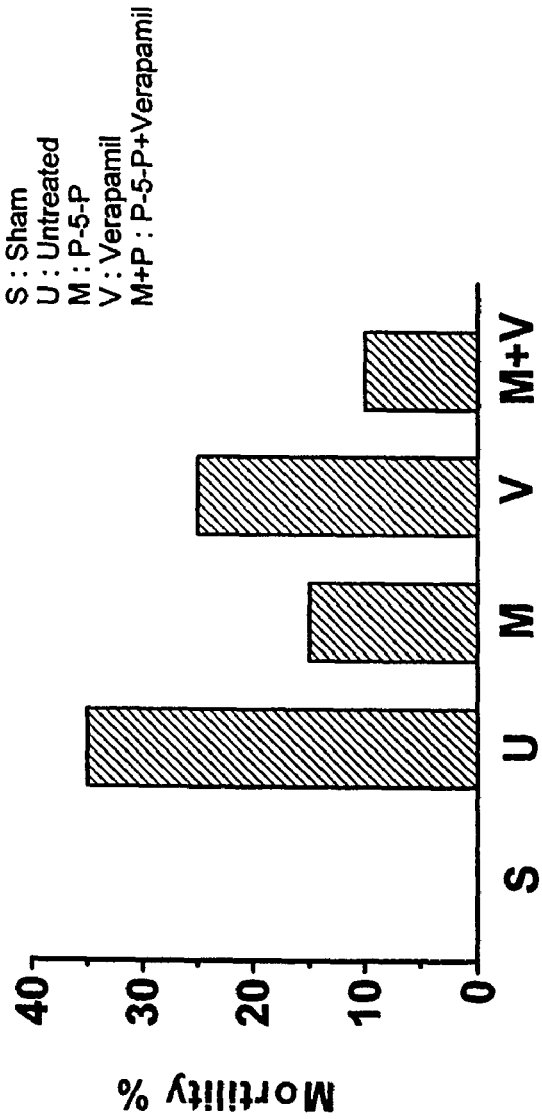
FIG. 4 is a graph showing the effect of P-5-P and verapamil, alone or in combination, on mortality in the rat model of coronary ligation.
Figure 5:
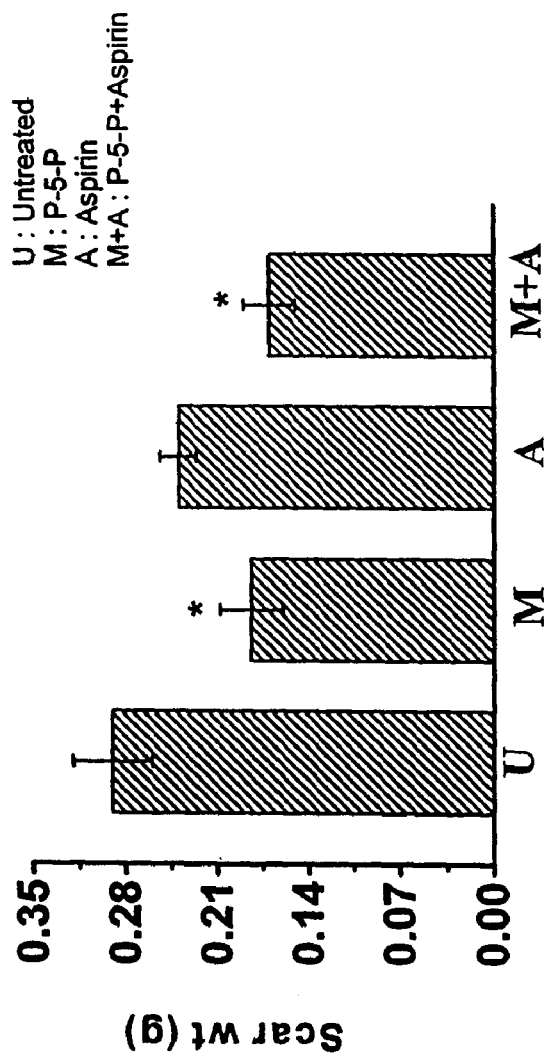
FIG. 5 is a graph showing the effect of P-5-P and aspirin, alone or in combination, on scar weight in the rat model of coronary ligation.
Figure 6:
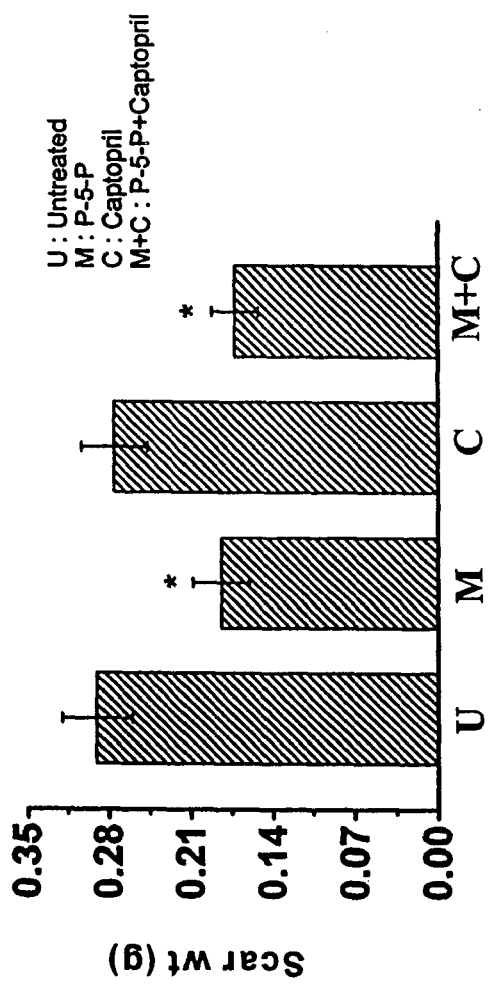
FIG. 6 is a graph showing the effect of P-5-P and captopril, alone or in combination, on scar weight in the rat model of coronary ligation.
Figure 7:
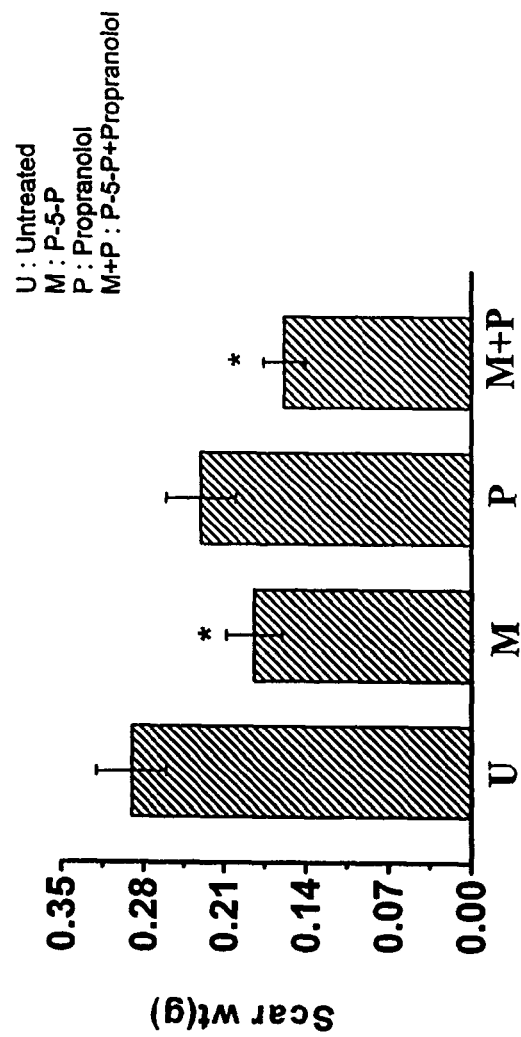
FIG. 7 is a graph showing the effect of P-5-P and propranolol, alone or in combination, on scar weight in the rat model of coronary ligation.
Figure 8:
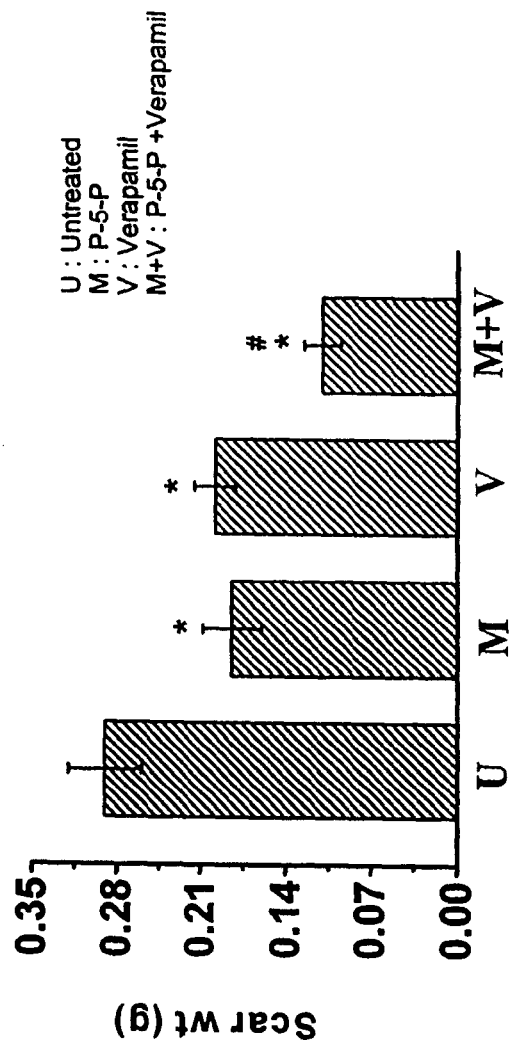
FIG. 8 is a graph showing the effect of P-5-P and verapamil, alone or in combination, on scar weight in the rat model of coronary ligation.
Figure 9:
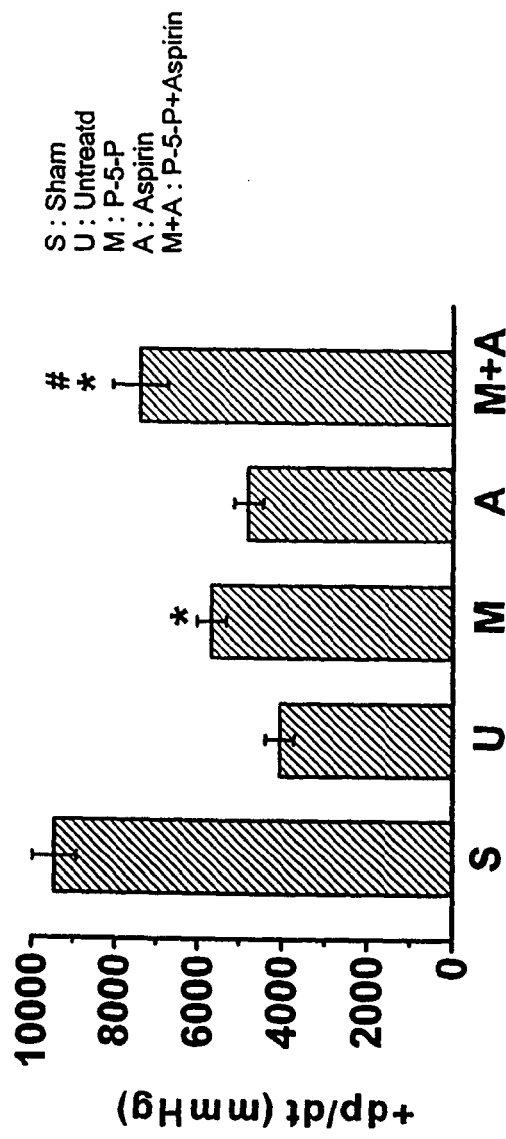
FIG. 9 is a graph showing the effect of P-5-P and aspirin, alone or in combination, on the rate of force of contraction (+dp/dt) in the rat model of coronary ligation.
Figure 10:
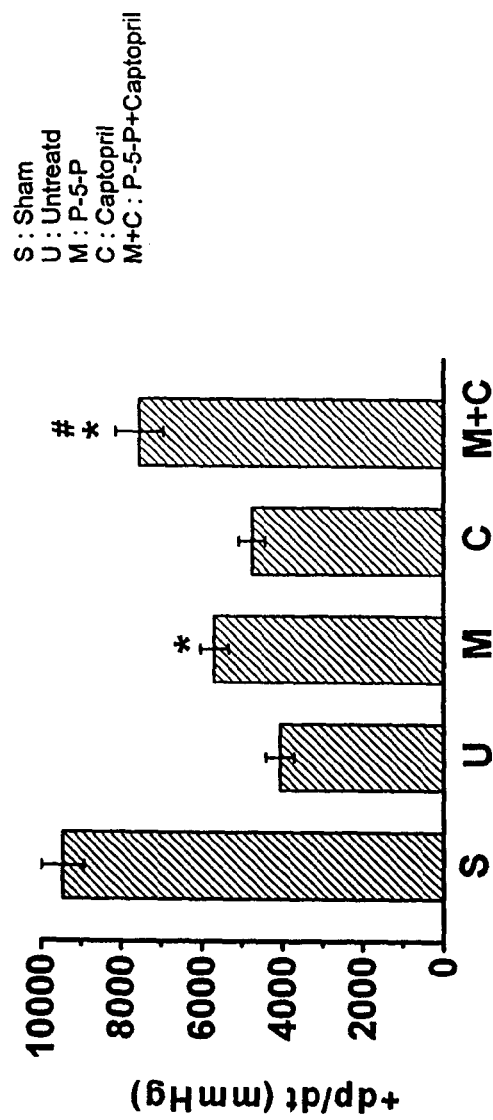
FIG. 10 is a graph showing the effect of P-5-P and captopril, alone or in combination, on the rate of force of contraction (+dp/dt) in the rat model of coronary ligation.
Figure 11:
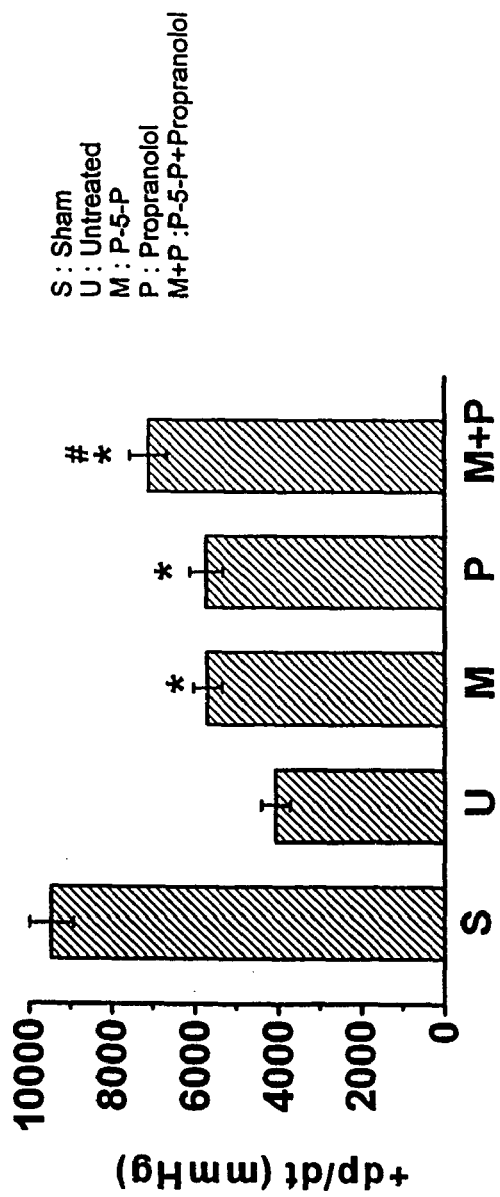
FIG. 11 is a graph showing the effect of P-5-P and propranolol, alone or in combination, on the rate of force of contraction (+dp/dt) in the rat model of coronary ligation.
Figure 12:
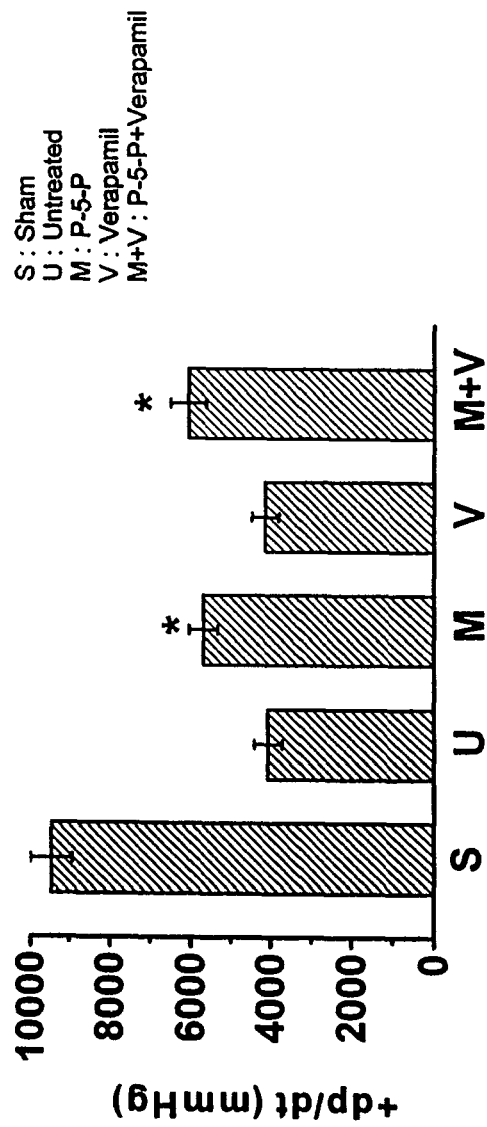
FIG. 12 is a graph showing the effect of P-5-P verapamil, alone or in combination, on the rate of force of contraction (+dp/dt) in the rat model of coronary ligation.
Figure 13:
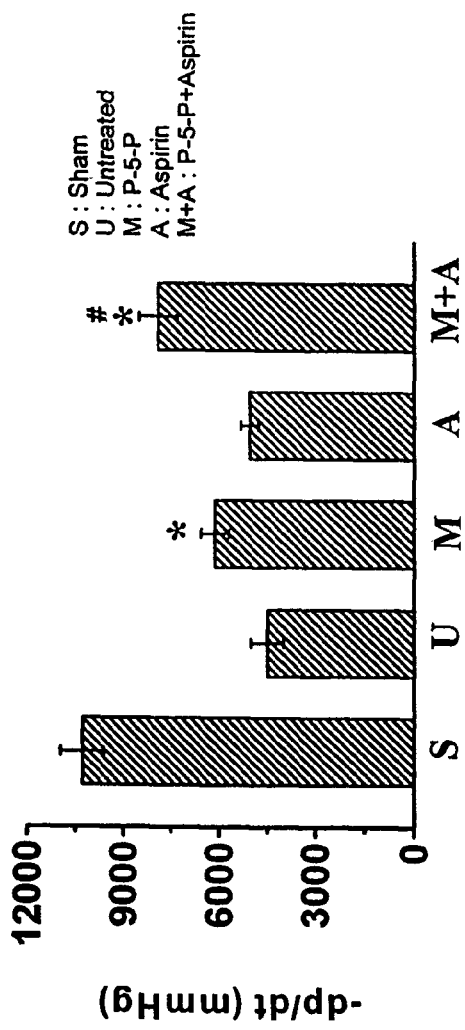
FIG. 13 is a graph showing the effect of P-5-P and aspirin, alone or in combination, on the rate of force of relaxation (−dp/dt) in the rat model of coronary ligation.
Figure 14:
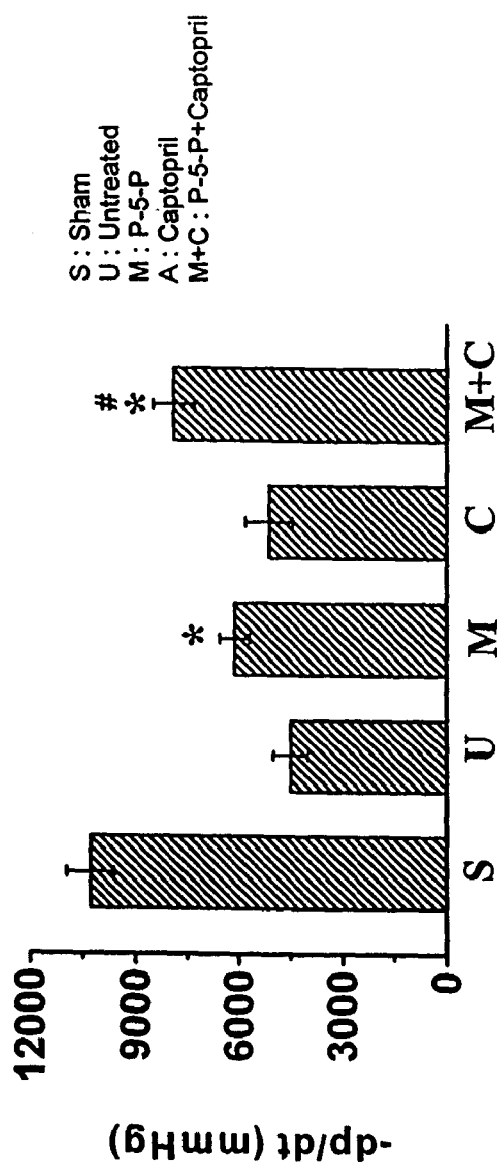
FIG. 14 is a graph showing the effect of P-5-P and captopril, alone or in combination, on the rate of force of relaxation (−dp/dt) in the rat model of coroary ligation.
Figure 15:
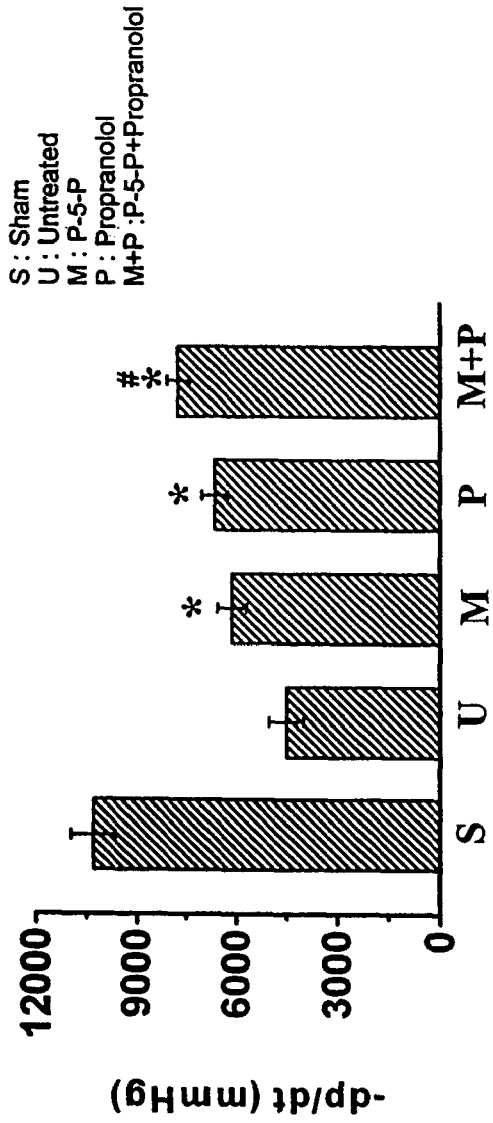
FIG. 15 is a graph showing the effect of P-5-P and propranolol, alone or in combination, on the rate of force of relaxation (−dp/dt) in the rat model of coronary ligation.
Figure 16:
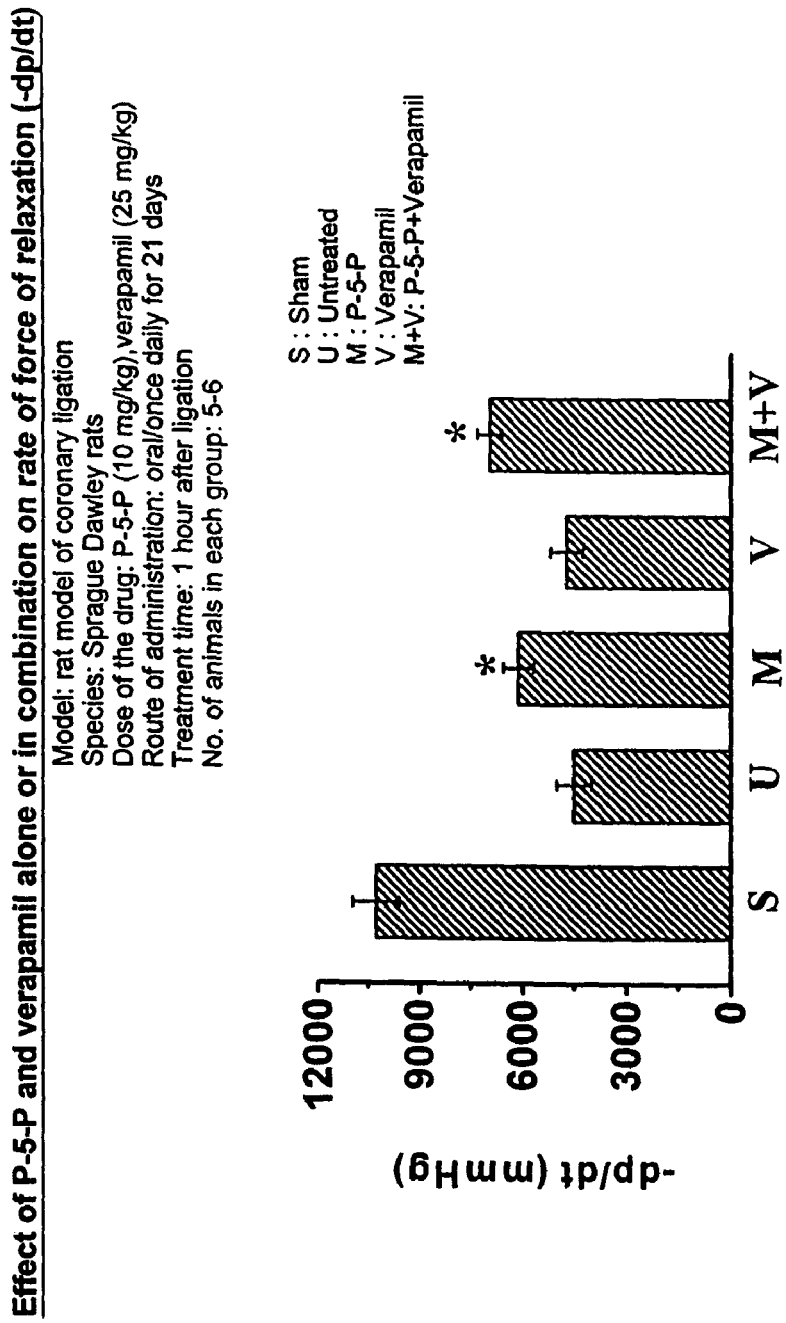
FIG. 16 is a graph showing the effect of P-5-P and verapamil, alone or in combination, on the rate of force of relaxation (−dp/dt) in the rat model of coronary ligation.
Figure 17:
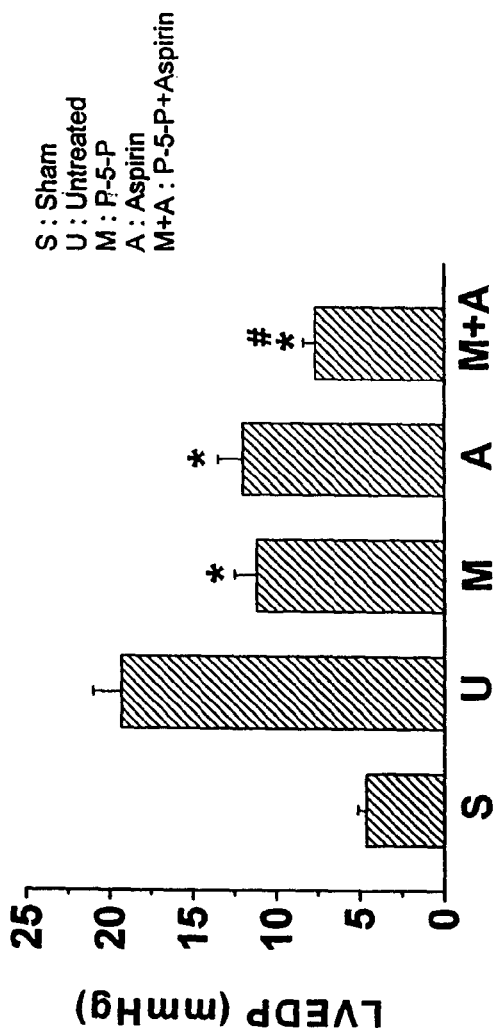
FIG. 17 is a graph showing the effect of P-5-P and aspirin, alone or in combination, on left ventricular end diastolic pressure (LVEDP) in the rat model of coronary ligation.
Figure 18:
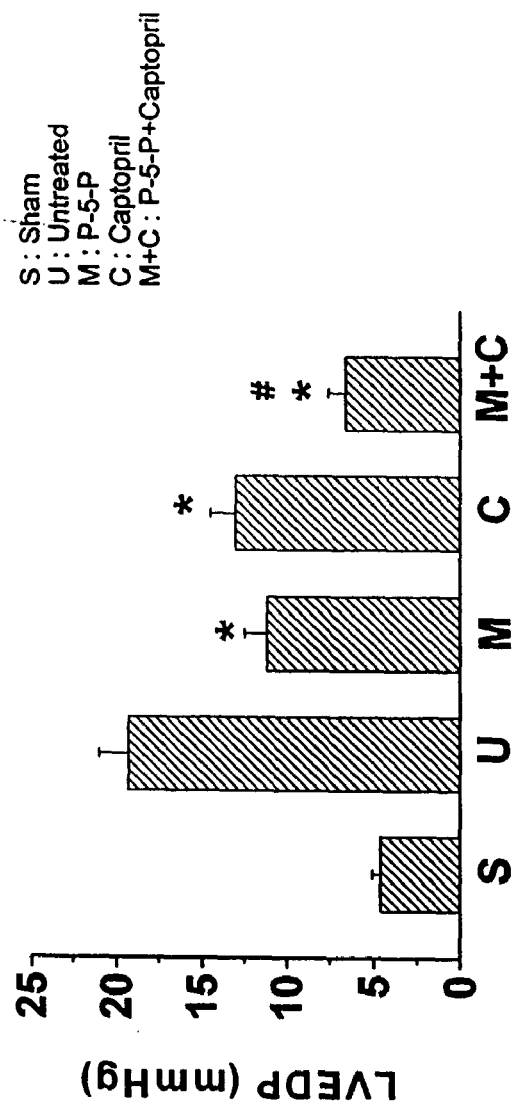
FIG. 18 is a graph showing the effect of P-5-P and captopril, alone or in combination, on left ventricular end diastolic pressure (LVEDP) in the rat model of coronary ligation.
Figure 19:
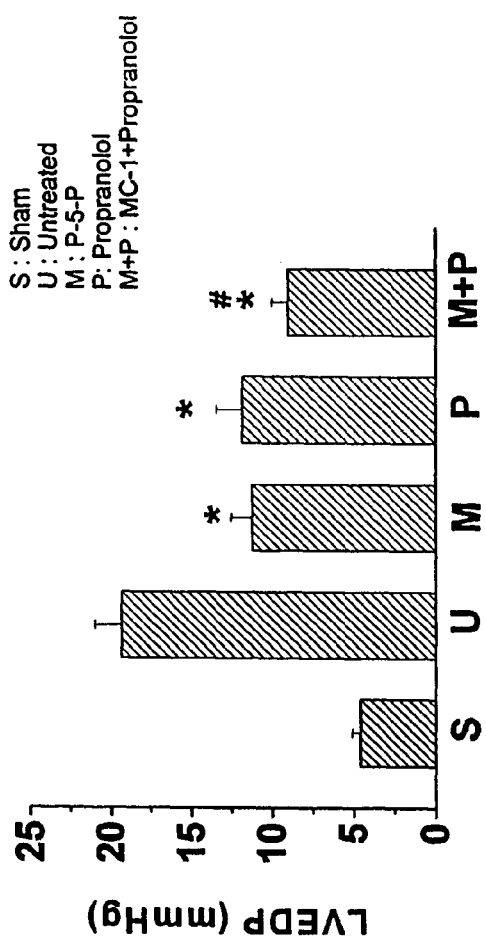
FIG. 19 is a graph showing the effect of P-5-P and propranolol, alone or in combination, on left ventricular end diastolic pressure (LVEDP) in the rat model of coronary ligation.
Figure 20:
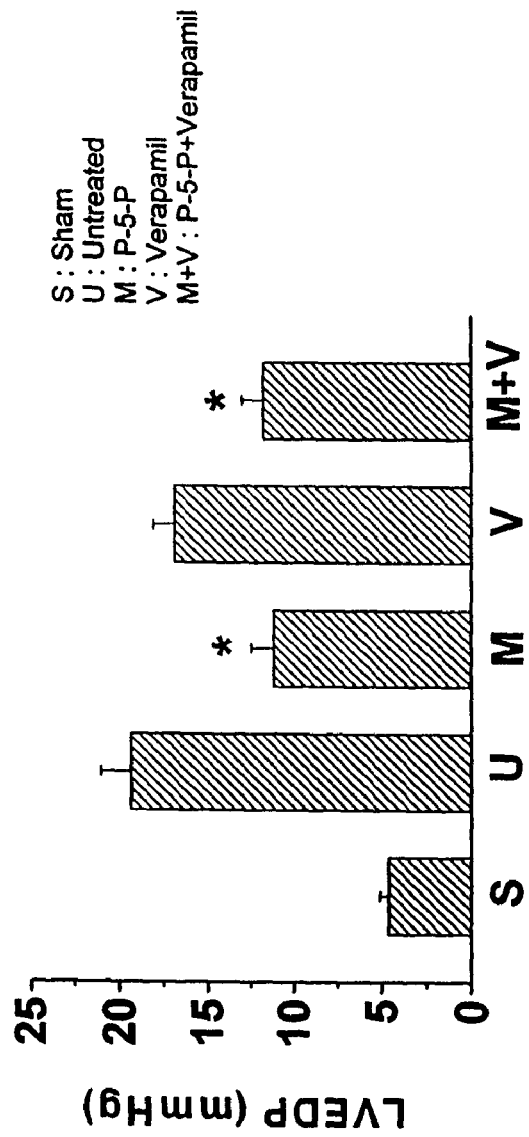
FIG. 20 is a graph showing the effect of P-5-P and verapamil, alone or in combination, on left ventricular end diastolic pressure (LVEDP) in the rat model of coronary ligation.
Figure 21:
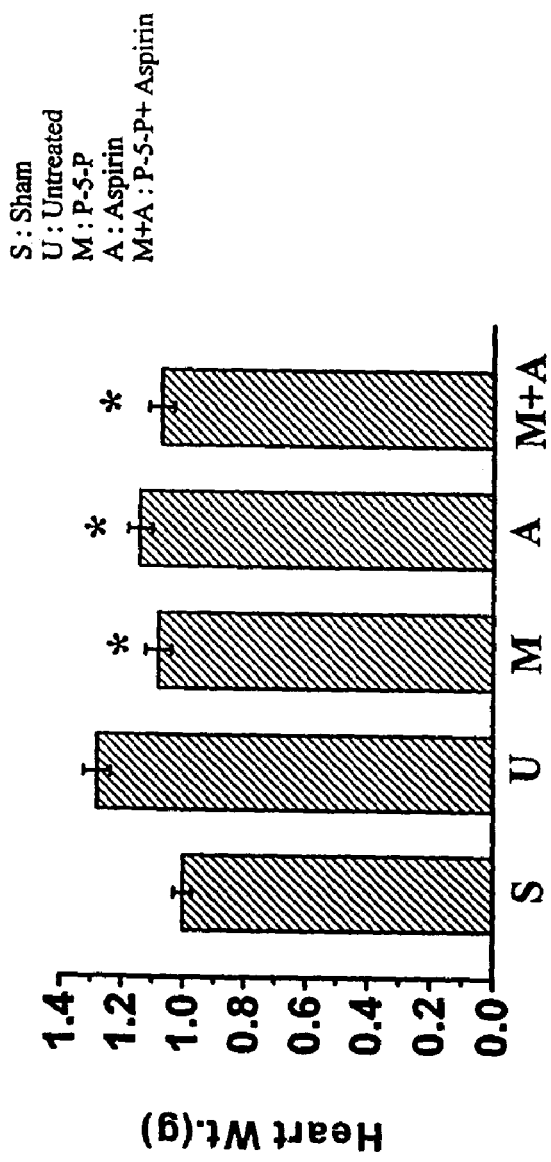
FIG. 21 is a graph showing the effect of P-5-P and aspirin, alone or in combination, on heart weight in the rat model of coronary ligation.
Figure 22:
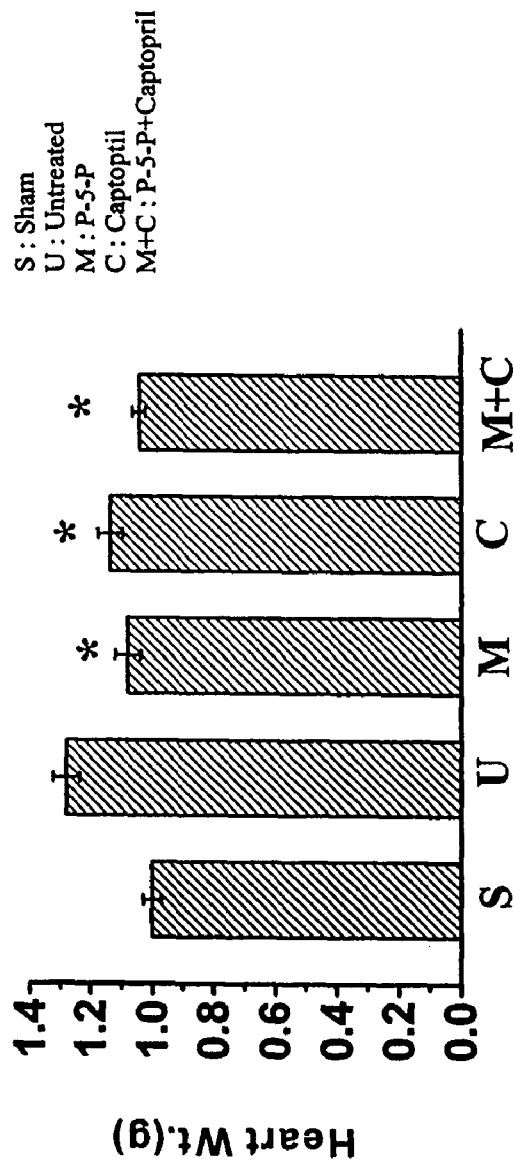
FIG. 22 is a graph showing the effect of P-5-P and captopril, alone or in combination, on heart weight in the rat model of coronary ligation.
Figure 23:
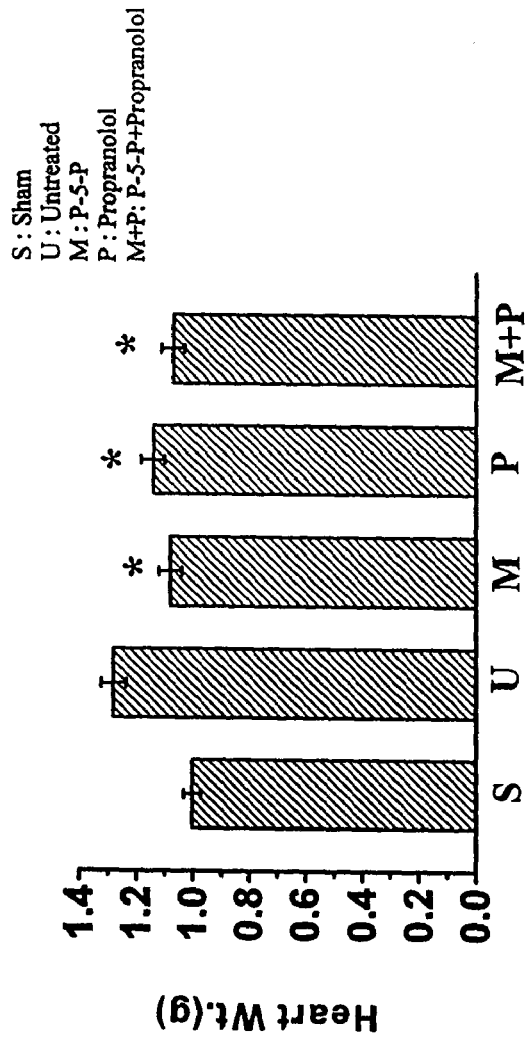
FIG. 23 is a graph showing the effect of P-5-P propranolol, alone or in combination, on heart weight in the rat model of coronary ligation.
Figure 24:
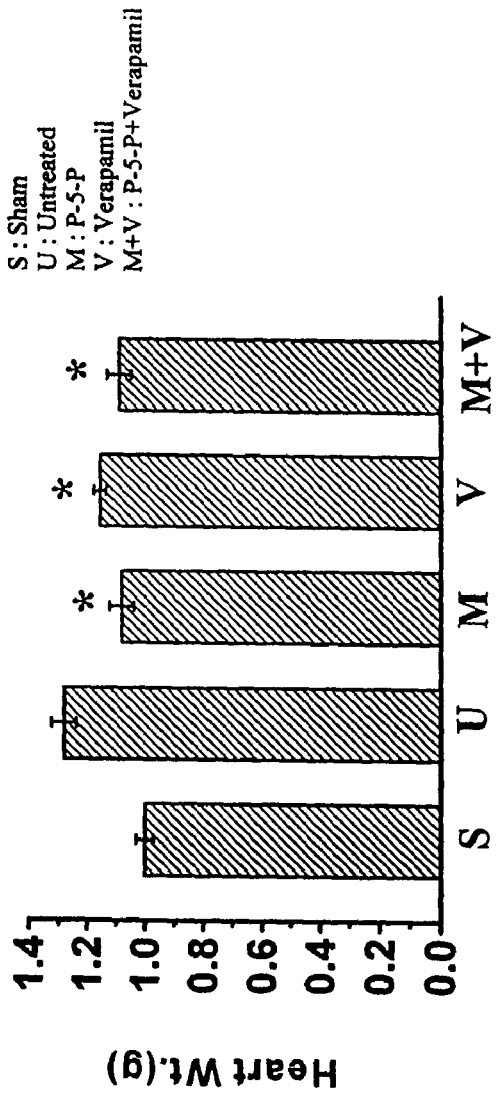
FIG. 24 is a graph showing the effect of P-5-P and verapamil, alone or in combination, on heart weight in the rat model of coronary ligation.
Figure 25:
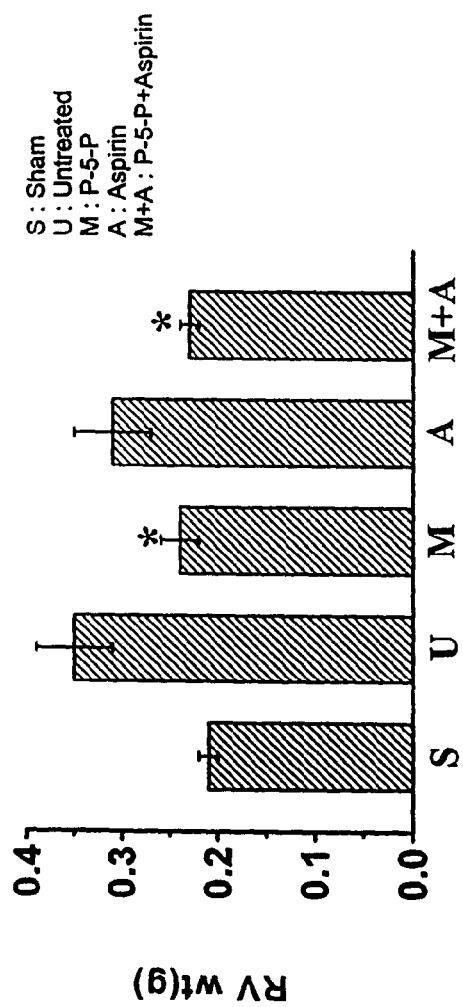
FIG. 25 is a graph showing the effect of P-5-P and aspirin, alone or in combination, on right ventricular weight in the rat model of coronary ligation.
Figure 26:
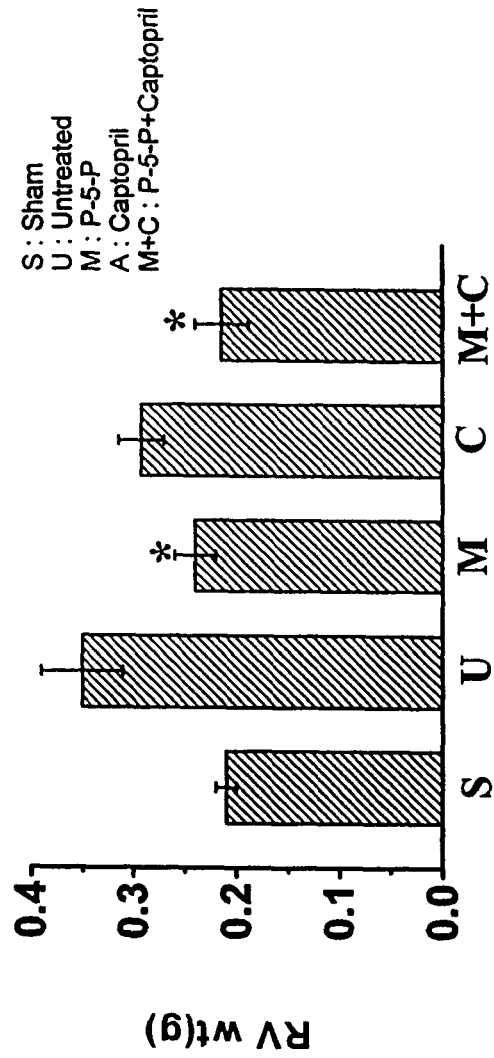
FIG. 26 is a graph showing the effect of P-5-P and captopril, alone or in combination, on right ventricular weight in the rat model of coronary ligation.
Figure 27:
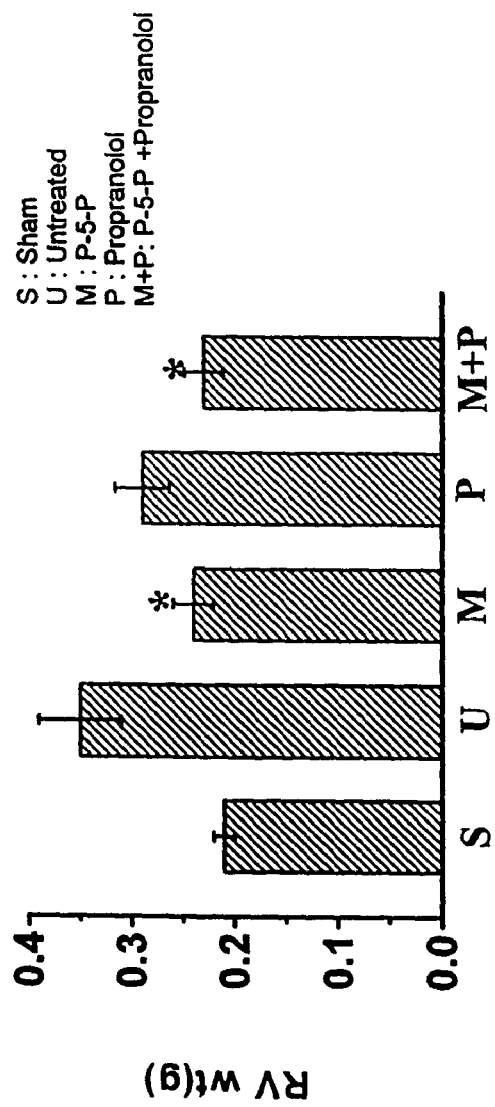
FIG. 27 is a graph showing the effect of P-5-P and propranolol, alone or in combination, on right ventricular weight in the rat model of coronary ligation.
Figure 28:
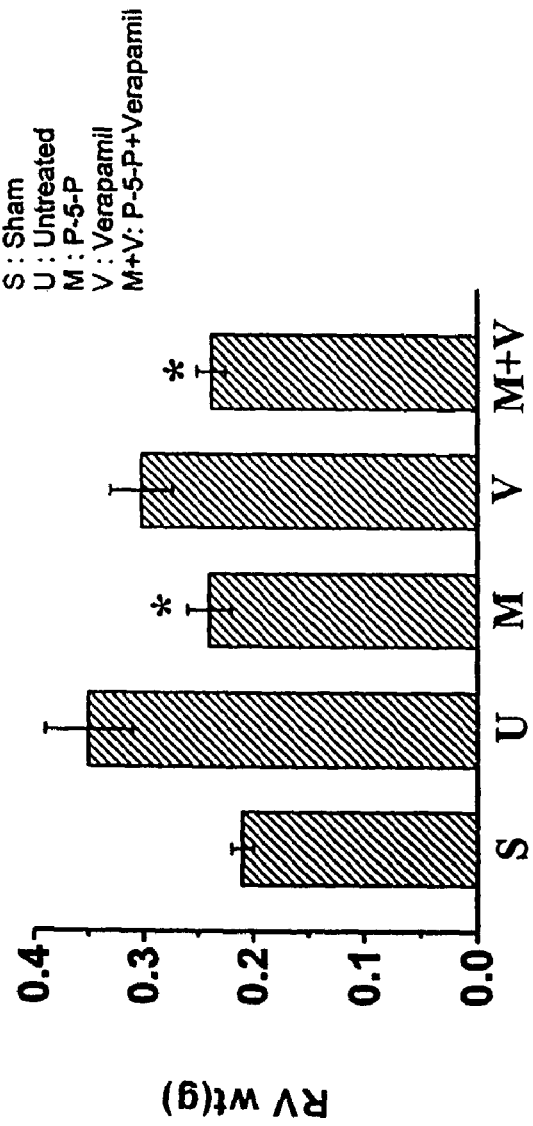
FIG. 28 is a graph showing the effect of P-5-P and verapamil, alone or in combination, on right ventricular weight in the rat model of coronary ligation.

Acute myocardial infarction resulted in a total mortality of 35% % in the untreated group of rats in 21 days. The highest mortality occurred within the first 2 days following occlusion. As compared to the untreated group, treatment with P-5-P, verapamil, or P-5-P and verapamil showed lower mortality rates of 15%, 25%, 10%, respectively (FIG. 4).

In addition to captopril, other angiotensin converting enzyme inhibitors, such as, for example, enalapril or imidapril, can similarly be administered in place of captopril. In addition to verapamil, other known calcium channel blockers, such as, for example, nifedipine or diltiazem, can similarly be administered in place of verapamil. In addition to propranolol, other β-adrenergic receptor antagonists such as, for example, atenolol, timolol, and metoprolol can similarly be administered in place of propranolol. In addition to aspirin, other antithrombolytic agents such as, for example, antiplatelet agents and heparin can similarly be administered in place of aspirin. Additionally, angiotensin II receptor antagonists such as, for example, losartan and valsartan can be used in the above example.

These animals are used in Examples 11 and 12 below. For EKG studies, these animals are used as their controls before surgery, so that before surgery is done on these animals EKG traces are taken which are then used as controls for the same animals after surgery.

Example 11

In Vivo—Hemodynamic Changes

The animals are prepared and grouped as described in Example 10 and were anesthetized with a solution of ketamine/xylazine which was injected. To maintain adequate ventilation, the trachea was intubated; the right carotid artery was exposed for introducing a microtip pressure transducer (model SPR-249, Millar, Houston, Tex.) into the left ventricle. The catheter was secured with a silk ligature around the artery, and various hemodynamic parameters such as left ventricular systolic pressure (LVSP), left ventricular end diastolic pressure (LVEDP), rate of contraction (+dp/dt), rate of relaxation (−dP/dt) were recorded and calculated on a computer system using a Acknowledge 3.1 software.

Once the hemodynamic parameters were measured the animals were sacrificed and hearts removed for measurement of heart weight, right ventricular weight, left ventricular weight and scar weight. Because complete healing of the scar in rats after coronary occlusion requires approximately 3 weeks, scar weight were measured only at 21 days.

FIGS. 5–8 demonstrate that the occlusion of coronary artery in rats for 21 days produces a significant scar evident by scar weight. Furthermore, FIGS. 5–8 demonstrate that P-5-P has a significant beneficial effect on scar weight in groups where P-5-P treatment is either given alone or in combination with verapamil, aspirin, captopril, or propranolol, respectively.

FIGS. 9–12 demonstrate that P-5-P has a significant beneficial effect on rate of contraction (+dP/dt) in groups where P-5-P treatment is either given alone or in combination with verapamil, aspirin, captopril, or propranolol, respectively.

FIGS. 13–16 demonstrate that P-5-P has a significant beneficial effect on rate of relaxzation (+dP/dt) in groups where P-5-P treatment is either given alone or in combination with verapamil, aspirin, captopril, or propranolol, respectively.

FIGS. 17–20 demonstrate that P-5-P has a significant beneficial effect on rate of left ventricular end diastolic pressure (LVEDP) in groups where P-5-P treatment is either given alone or in combination with verapamil, aspirin, captopril, or propranolol, respectively.

FIGS. 21–24 demonstrate that P-5-P has a significant beneficial effect on whole heart weight in groups where P-5-P treatment is either given alone or in combination with verapamil, aspirin, captopril, or propranolol, respectively.

FIGS. 25–28 demonstrate that P-5-P has a significant beneficial effect on right ventricular weight in groups where P-5-P treatment is either given alone or in combination with verapamil, aspirin, captopril, or propranolol, respectively.

In addition to captopril, other angiotensin converting enzyme inhibitors, such as, for example, enalapril or imidapril, can similarly be administered in place of captopril. In addition to verapamil, other known calcium channel blockers, such as, for example, nifedipine or diltiazem, can similarly be administered in place of verapamil. In addition to propranolol, other β-adrenergic receptor antagonists such as, for example, atenolol, timolol, and metoprolol can similarly be administered in place of propranolol. In addition to aspirin, other antithrombolytic agents such as, for example, antiplatelet agents and heparin can similarly be administered in place of aspirin. Additionally, angiotensin II receptor antagonists such as, for example, losartan and valsartan can be used in the above example.

Example 12

In Vivo—Hypertension

It has been well demonstrated by various investigators that feeding 8–10% sucrose in water induces hypertension in rats. Zein et al., in their publication entitled Sugar-Induced Blood Pressure Elevations Over the Lifespan of Three Substrains of Wistar Rats in Am. Coll. Nutr., 17 (1), 36–37, 1998, have shown that high dietary sucrose can chronically increase systolic blood pressure (SBP) in three substrains of Wistar rats. Increased concentrations of circulating insulin were found in Wistar Kyoto rats and Munich Wistar rats suggesting that the glucose/insulin system was involved, at least in these two substrains, in the maintenance of high SBP levels during chronic, heavy sugar ingestion. Hulman et al. in their publication entitled The Effect of Excess Dietary Sucrose on Growth, Blood Pressure, and Metabolism in Developing Sprague-Dawley Rats in Pediatr. Res., 36:95–101, have shown that consumption of a diet in which complex carbohydrate has been replaced by sucrose causes both elevated blood pressure and insulin resistance in juvenile rats with no genetic predisposition in either condition. Although blood pressure increased with increasing age and body weight in all four diet groups, higher blood pressures were clearly correlated with the sucrose diet in both males and females. The higher blood pressure cannot be explained by greater total body weight in the sucrose-fed animals, because there was no difference in weight between control-fed and sucrose-fed rats in each sex group. Reaven et al., in their publication entitled Sugar-Induced Hypertension in Sprague-Dawley Rats in Am. J. Hypertens; 1991:610–614, have shown that the ability of simple sugars to increase plasma insulin and TG concentration and raise blood pressure is not unique to fructose, but can also be seen when Sprague-Dawley rats eat diets enriched with either glucose or sucrose. Since plasma glucose concentrations did not change, it is assumed that glucose-fed and sucrose-fed Sprague-Dawley rats also became more resistant to insulin-stimulated glucose uptake. In applying this model, the concurrent administration of pyridoxal-5'-phosphate and captopril or verapamil significantly decreases the sucrose-induced increase in systolic blood pressure (SBP).

The blood pressure is monitored using the tail cuff method. The SBP is detected on an amplifier and the Acknowledge™ computer software program is used to determine the calculations.

The effect of concurrent administration of pyridoxal-5'-phosphate and captopril or verapamil on systolic blood pressure (marker of hypertension) in 10% sucrose induced hypertension in rats is determined.

Figure 29A:
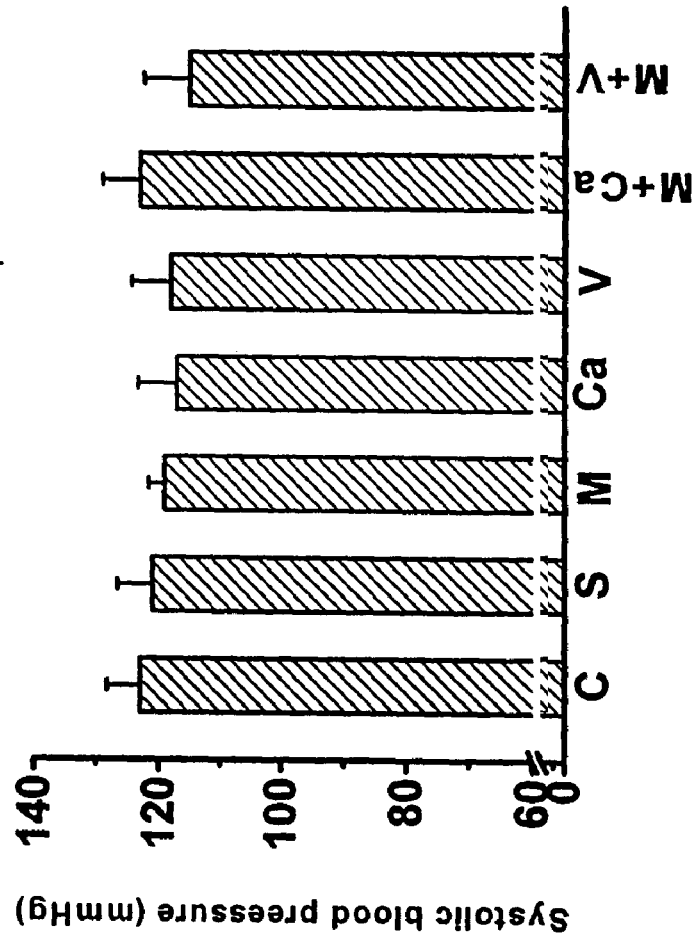
FIG. 29A is a graph showing systolic blood pressure in rats from all pretreatment experiment groups at "0" day. "C" designates a control group; "S" designates a sucrose diet induced diabetic group; "M" designates a group administered P-5-P alone; "Ca" designates a group administered captopril alone; "V" designates a group administered verapamil alone; "M+Ca" designates a group administered P-5-P and captopril; "M+V" designates a group administered P-5-P and verapamil.

FIGS. 29A and 9B demonstrate that P-5-P has a significant beneficial effect on systolic blood pressure in groups where P-5-P treatment is either given alone or in combination with verapamil or captopril 1 week prior to inducing hypertension in rats with a sucrose diet.

Figure 29B:
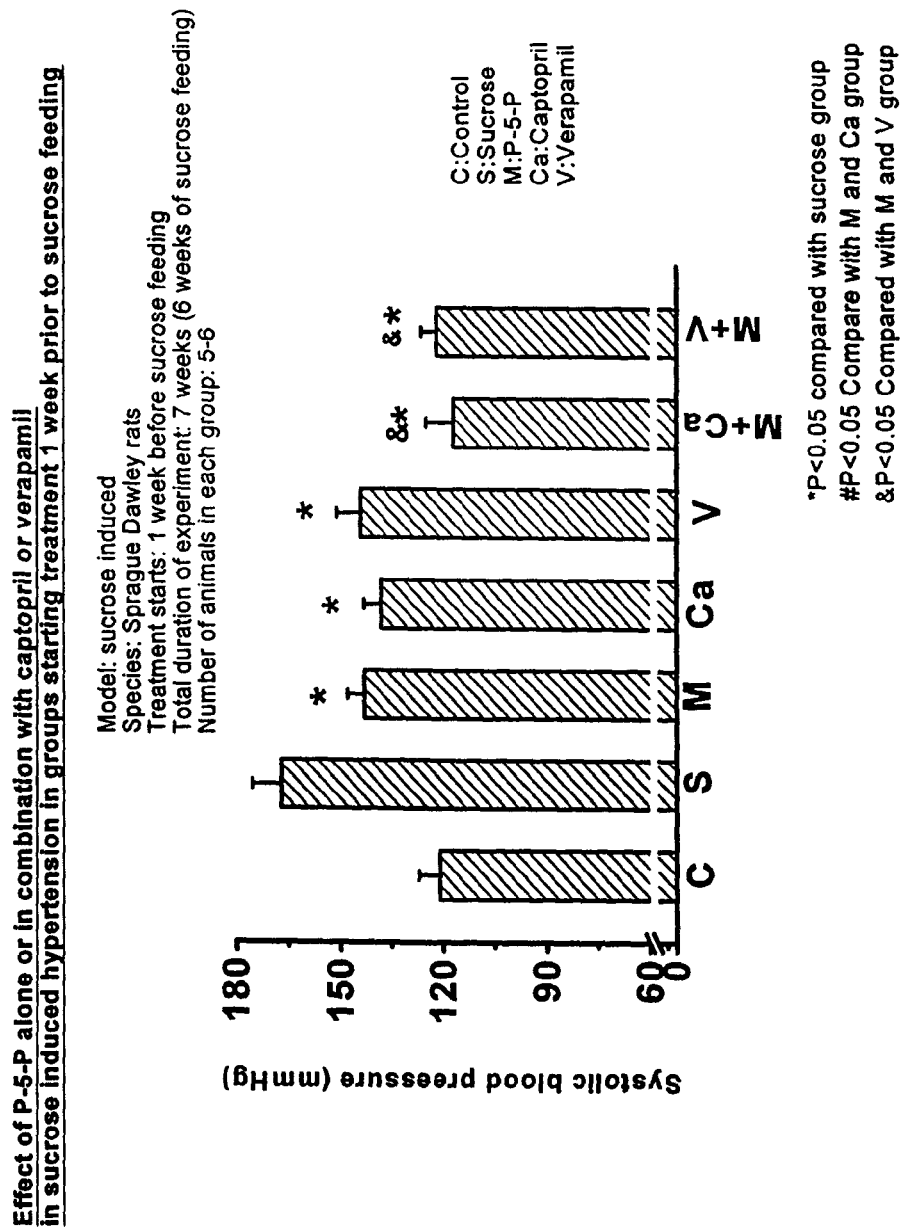
FIG. 29B is a graph showing the effect of pretreatment with P-5-P, captopril and verapamil on systolic blood pressure in rats when administered 1 week prior to sucrose diet induced diabetes. "C", "S", "M", "Ca", "V", "M+Ca", and "M+V" are designated as in FIG. 29A.

FIGS. 29A and 29B demonstrate that P-5-P has a significant beneficial effect on systolic blood pressure in groups where P-5-P treatment is either given alone or in combination with verapamil or captopril 1 week prior to inducing hypertension in rats with a sucrose diet.

Figure 30A:
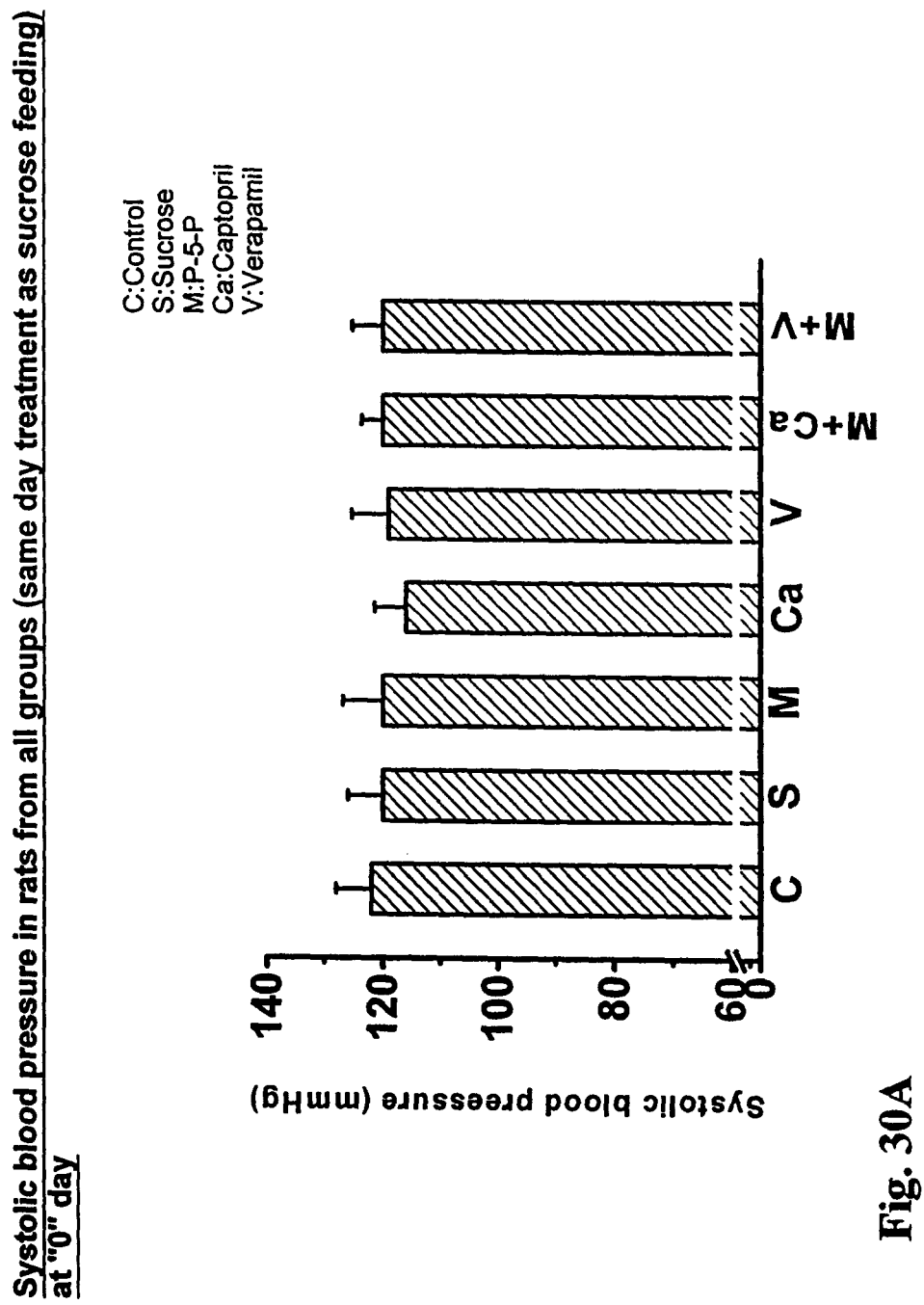
FIG. 30A is a graph showing systolic blood pressure in rats from all experiment groups involved in same day treatment as sucrose feeding at "0" day. "C", "S", "M", "Ca", "V", "M+Ca", and "M+V" are designated as in FIG. 29A.
Figure 30B:
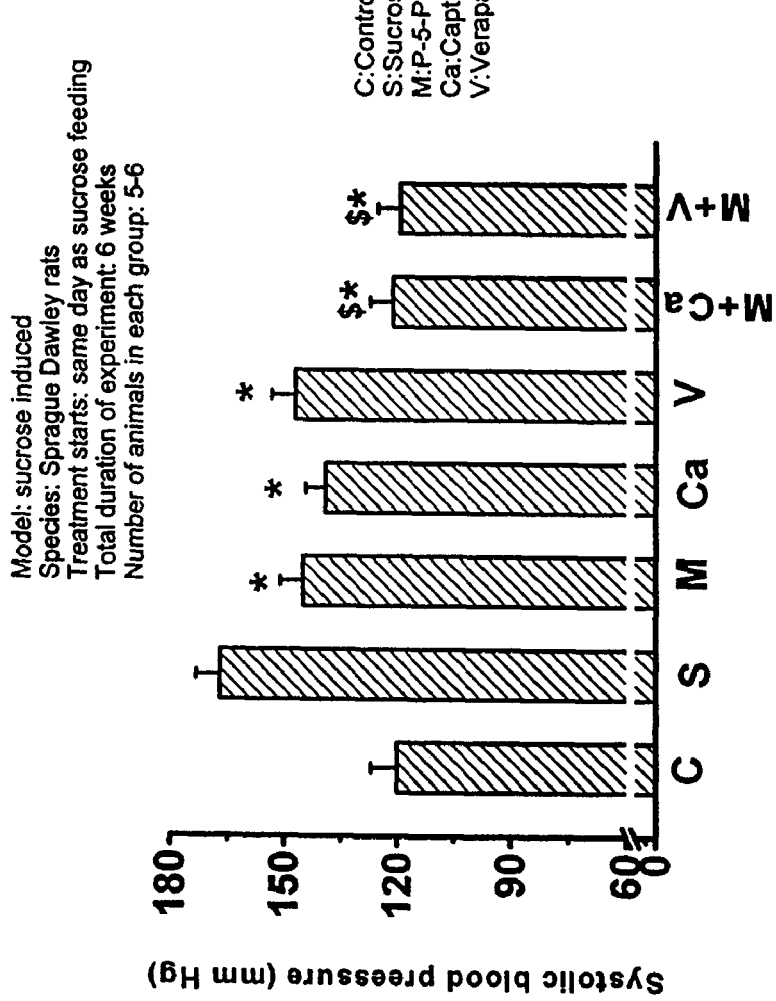
FIG. 30B is a graph showing the effect of administration of P-5-P, captopril and verapamil on systolic blood pressure in rats when administered the same day as sucrose feeding to induce diabetes. "C", "S", "M", "Ca", "V", "M+Ca", and "M+V" are designated as in FIG. 29A.

FIGS. 30A and 30B demonstrate that P-5-P has a significant beneficial effect on systolic blood pressure in groups where P-5-P treatment is either given alone or in combination with verapamil or captopril the same day as inducing hypertension in rats with a sucrose diet.

Figure 31A:
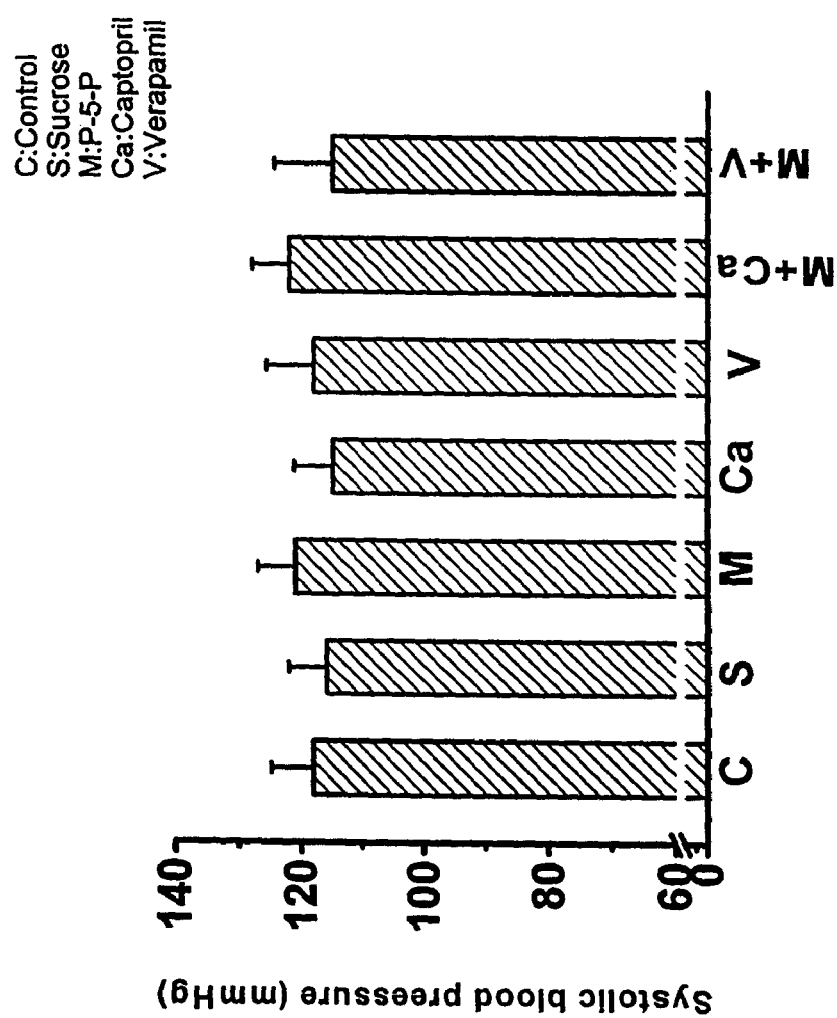
FIG. 31A is a graph showing systolic blood pressure in rats from all experiment groups involved in treatment two weeks after sucrose feeding at "0" day. "C", "S", "M", "Ca", "V", "M+Ca", and "M+V" are designated as in FIG. 29A.
Figure 31B:
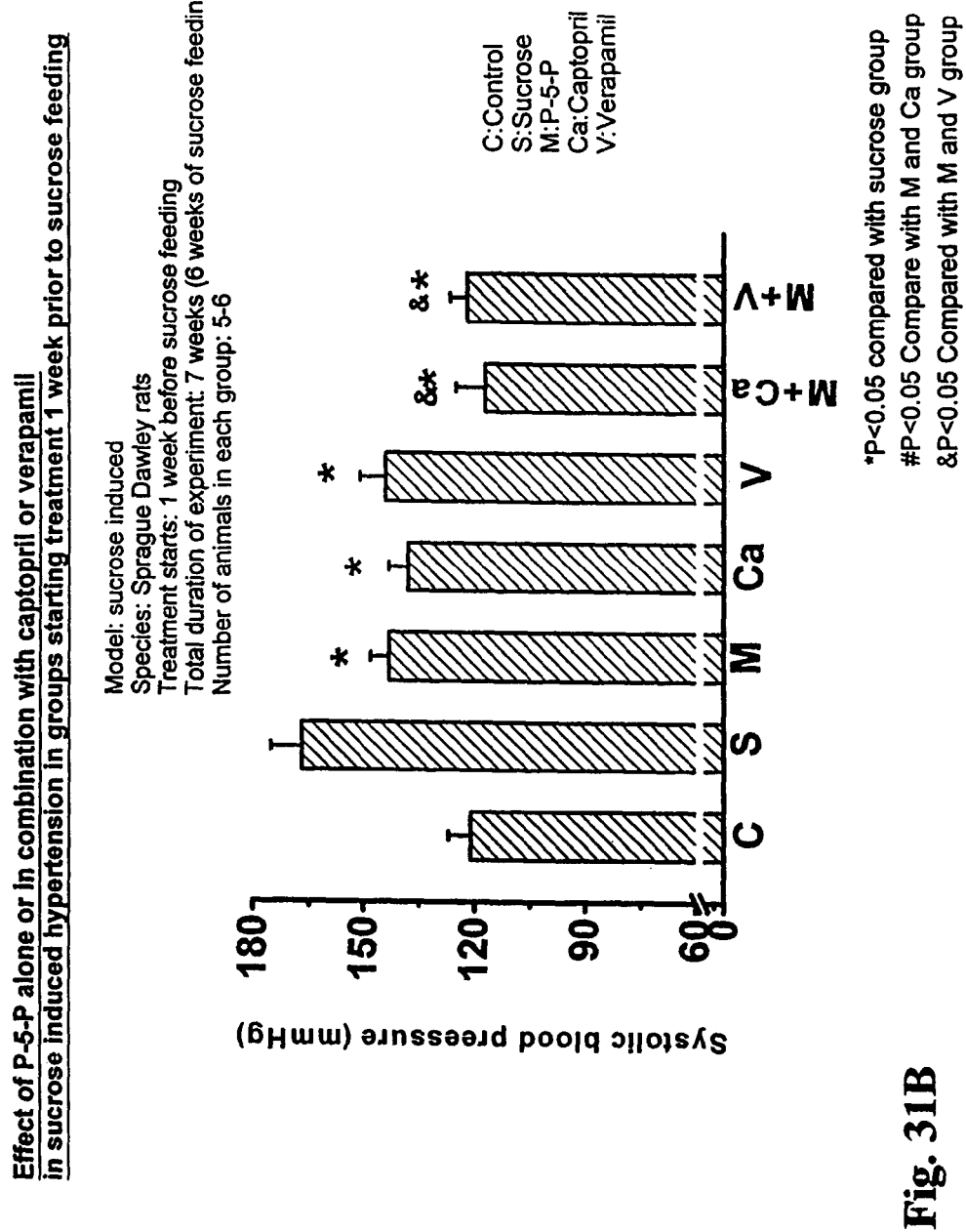
FIG. 31B is a showing systolic blood pressure in rats from all experiment groups involved in treatment two weeks after sucrose feeding at "0" day. "C", "S", "M", "Ca", "V", "M+Ca", and "M+V" are designated as in FIG. 29A.

FIGS. 31A and 31B demonstrate that P-5-P has a significant beneficial effect on systolic blood pressure in groups where P-5-P treatment is either given alone or in combination with verapamil or captopril two weeks after inducing hypertension in rats with a sucrose diet.

In addition to captopril, other angiotensin converting enzyme inhibitors, such as, for example, enalapril or imidapril, can similarly be administered in place of captopril. In addition to verapamil, other known calcium channel blockers, such as, for example, nifedipine or diltiazem, can similarly be administered in place of verapamil. In addition to propranolol, other β-adrenergic receptor antagonists such as, for example, atenolol, timolol, and metoprolol can similarly be administered in place of propranolol. Additionally, angiotensin II receptor antagonists such as, for example, losartan and valsartan can be used in the above example.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

We claim:

1. A method of treating congestive heart failure in a mammal comprising: concurrently administering to the mammal a therapeutically effective amount for treating congestive heart failure of a combination of a compound selected from the group consisting of pyridoxal-5'-phosphate, pyridoxal, pyridoxamine, a 3-acylated pyridoxal analogue, a pharmaceutically acceptable acid addition salt thereof, and a mixture thereof, and a therapeutic cardiovascular compound selected from the group consisting of an angiotensin converting enzyme inhibitor, an angiotensin II receptor antagonist, a vasodilator, a diuretic, an α-adrenergic receptor antagonist, and a mixture thereof, wherein the 3-acylated pyridoxal analogue is a compound of the formula

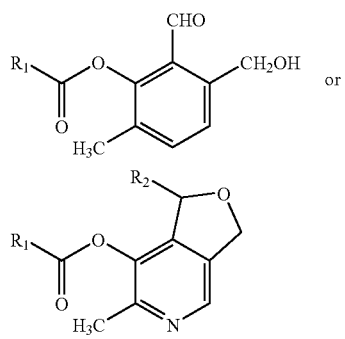

wherein
$R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group; and
$R_2$ is a secondary amino group.

2. A method according to claim 1, wherein the angiotensin converting enzyme inhibitor is captopril, enalapril, lisinopril, benazapril, fosinopril, quinapril, ramipril, spirapril, imidapril, or moexipril.

3. A method according to claim 1, wherein the angiotensin II receptor antagonist is losartan or valsartan.

4. A method according to claim 1, wherein the vasodilator is hydralazine, nitroglycerin, or isosorbide dinitrate.

5. A method according to claim 1, wherein the diuretic is furosemide, diuril, amiloride, or hydrodiuril.

6. A method according to claim 1, wherein the compound is administered enterally or parenterally and the therapeutic cardiovascular compound is administered enterally or parenterally.

7. A method according to claim 1, wherein the compound and the therapeutic cardiovascular compound are administered in a single dosage form.

8. A method according to claim 1, wherein the α-adrenergic receptor antagonist is prazosin, doxazocin or labetalol.

9. A method according to claim 1, wherein the antioxidant is vitamin E, vitamin C or an isoflavone.

10. A method of treating congestive heart failure in a mammal comprising: concurrently administering to the mammal a therapeutically effective amount for treating congestive heart failure of a combination of a therapeutic cardiovascular compound selected from the group consisting of a calcium channel blocker, a β-adrenergic receptor antagonist, and a mixture thereof, and a compound selected from the group consisting of pyridoxal-5'-phosphate, pyridoxal, pyridoxamine, a 3-acylated pyridoxal analogue, a pharmaceutically acceptable acid addition salt thereof, and a mixture thereof, wherein the 3-acylated pyridoxal analogue is a compound of the formula

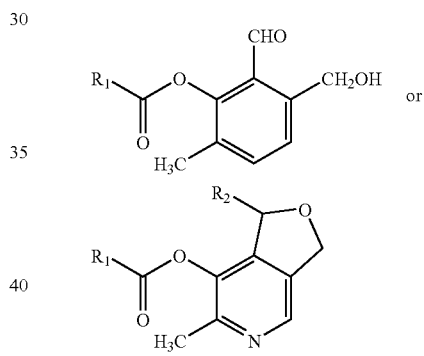

wherein
$R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group; and
$R_2$ is a secondary amino group.

11. A method according to claim 10, wherein the calcium channel blocker is verapamil, diltiazem, nicardipine, nifedipine, amlodipine, felodipine, nimodipine, or bepridil.

12. A method according to claim 10, wherein the β-adrenergic receptor antagonist is atenolol, propranolol, timolol or metoprolol.

* * * * *

UNITED STATES PATENT AND TRADEMARK OFFICE
CERTIFICATE OF CORRECTION

PATENT NO. : 7,115,625 B2
APPLICATION NO. : 10/639950
DATED : October 3, 2006
INVENTOR(S) : Sethi et al.

It is certified that error appears in the above-identified patent and that said Letters Patent is hereby corrected as shown below:

Title Page (57) under "ABSTRACT", second line, "such congestive" should read --such as congestive--

Title Page (56) "OTHER PUBLICATIONS", "Fragley" should read --Fregly--

Title Page (56) "FOREIGN PATENTS", "DE 863754  5/1978" should read --BE 863754  5/1978--

Title Page (56) "OTHER PUBLICATIONS", Trezise reference, "vol. 259-300" should read --Vol. 259, No. 3, pp. 259-300--

Col. 14, line 15-16: "Hydroxymethylpyidine" should read --Hydroxymethylpyridine--

Col. 14, line 61: "dimethylcarbamovloxy" should read --dimethylcarbamoyloxy--

Col. 15, line 40: "$KH_2PO_4$" should read --$KH_2PO$--

Col. 15, line 41: "$MgSO_44$" should read --$MgSO_4$--

Col. 16, line 62: "mm" should read --min--

Claim 1, Col. 23, line 30: " 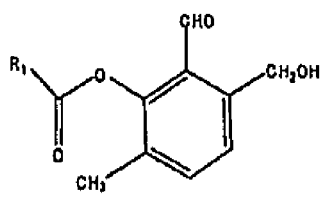 or" should read

-- 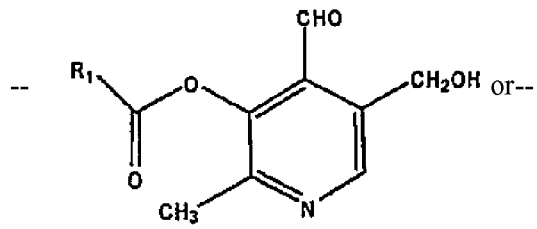 or--

UNITED STATES PATENT AND TRADEMARK OFFICE
CERTIFICATE OF CORRECTION

PATENT NO. : 7,115,625 B2  
APPLICATION NO. : 10/639950  
DATED : October 3, 2006  
INVENTOR(S) : Sethi et al.

It is certified that error appears in the above-identified patent and that said Letters Patent is hereby corrected as shown below:

Claim 10, Col. 23, line 30: " 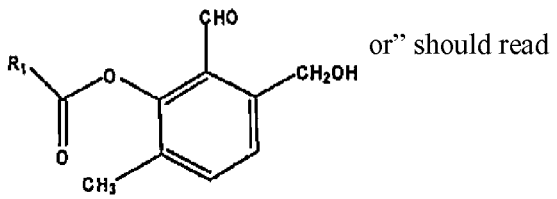 or" should read

-- 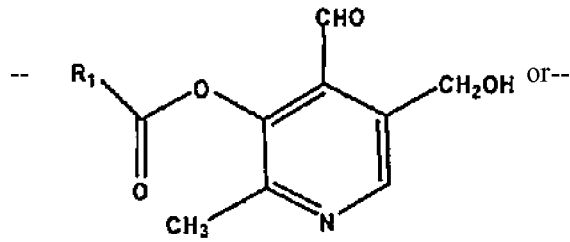 or--

Signed and Sealed this

Sixth Day of March, 2007

JON W. DUDAS  
*Director of the United States Patent and Trademark Office*

UNITED STATES PATENT AND TRADEMARK OFFICE
CERTIFICATE OF CORRECTION

PATENT NO.         : 7,115,625 B2                                      Page 1 of 1
APPLICATION NO. : 10/639950
DATED              : October 3, 2006
INVENTOR(S)        : Sethi et al.

It is certified that error appears in the above-identified patent and that said Letters Patent is hereby corrected as shown below:

Col. 15, line 40: "$KH_2PO_44$" should read --$KH_2PO_4$--

Signed and Sealed this

Third Day of July, 2007

JON W. DUDAS
*Director of the United States Patent and Trademark Office*